United States Patent
Le Garrec et al.

(10) Patent No.: US 12,350,260 B2
(45) Date of Patent: Jul. 8, 2025

(54) PROTEASE-ACTIVATED RECEPTOR-2 INHIBITORS FOR THE TREATMENT OF SENSORY NEUROPATHY INDUCED BY A MARINE NEUROTOXIC POISONING

(71) Applicants: Universite De Bretagne Occidentale, Brest (FR); Centre Hospitalier Regional Et Universitaire De Brest, Brest (FR); INSERM (Institut National De La Sante Et De La Recherche Medicale), Paris (FR)

(72) Inventors: Raphaele Le Garrec, Landunvez (FR); Killian L'Herondelle, Brest (FR); Laurent Misery, Plougastel (FR); Ophelie Pierre, Thiais (FR); Olivier Mignen, Logonna Daoulas (FR)

(73) Assignees: Universite De Bretagne Occidentale, Brest (FR); Centre Hospitalier Regional Et Universitaire De Brest, Brest (FR); INSERM (Institut National de la Santé et de la Recherche Médicale), Paris (FR)

( * ) Notice: Subject to any disclaimer, the term of this patent is extended or adjusted under 35 U.S.C. 154(b) by 843 days.

(21) Appl. No.: 17/600,977

(22) PCT Filed: Apr. 5, 2020

(86) PCT No.: PCT/EP2020/059698
§ 371 (c)(1),
(2) Date: Oct. 1, 2021

(87) PCT Pub. No.: WO2020/201572
PCT Pub. Date: Oct. 8, 2020

(65) Prior Publication Data
US 2022/0193048 A1    Jun. 23, 2022

(30) Foreign Application Priority Data

Apr. 5, 2019   (EP) .................................. 19305453

(51) Int. Cl.
| | |
|---|---|
| *A61K 31/454* | (2006.01) |
| *A61K 31/438* | (2006.01) |
| *A61K 38/05* | (2006.01) |
| *A61K 39/395* | (2006.01) |
| *A61K 45/00* | (2006.01) |
| *A61P 25/02* | (2006.01) |
| *C12N 5/071* | (2010.01) |
| *C12N 5/0793* | (2010.01) |
| *G01N 33/50* | (2006.01) |

(52) U.S. Cl.
CPC ............ *A61K 31/438* (2013.01); *A61K 38/05* (2013.01); *A61P 25/02* (2018.01); *C12N 5/062* (2013.01); *C12N 5/0629* (2013.01); *G01N 33/5023* (2013.01); *C12N 2501/11* (2013.01); *C12N 2501/13* (2013.01); *C12N 2501/33* (2013.01); *C12N 2501/999* (2013.01); *C12N 2502/083* (2013.01); *C12N 2502/094* (2013.01)

(58) Field of Classification Search
CPC ....... A61K 31/438; A61K 38/05; A61P 25/02; C12N 5/062; C12N 5/0629; C12N 2501/11; C12N 2501/13; C12N 2501/33; C12N 2501/999; C12N 2502/083; C12N 2502/094; G01N 33/5023
See application file for complete search history.

(56) References Cited

FOREIGN PATENT DOCUMENTS

| | | |
|---|---|---|
| EP | 1273913 A1 | 1/2003 |
| JP | 2013/021946 A | 2/2013 |
| JP | 2013/135637 A | 7/2013 |

OTHER PUBLICATIONS

Kempkes et al., "Role of PAR-2 in Neuroimmune Communication and Itch," Itch: mechanisms and treatment, chptr 11, 193-212 (2010) (Year: 2010).*
Tey et al., "Targeted treatment of pruritus: a look into the future," British Journal of dermatology 165:5-17 (2011) (Year: 2011).*
Cuypers et al., "TRPV1 as a key determinant in ciguatera and neurotoxic shellfish poisoning," Biochem Biophys Res Commun. 361(1):214-217 (2007) (Year: 2007).*
L'Herondelle et al "Study of the Involvement of Itch Mediators in the Neuropeptide Release Induced by Pacific- Ciguatoxin-2 in a Co-Culture Model of Sensory Neurons and Keratinocytes" Toxicon vol. 116, pp. 72-86, 2016.
Muley et al "Prophylactic Inhibition of Neutrophil Elastase Prevents the Development of Chronic Neuropathic Pain in Osteoarthritic Mice" Journal of Neuroinflammation vol. 14, pp. 168-179, 2017.
Ulmann et al "Trophic Effects of Keratinocytes on the Axonal Development of Sensory Neurons in a Coculture Model" European Journal of Neuroscience vol. 26, pp. 113-125, 2007.

* cited by examiner

*Primary Examiner* — Lianko G Garyu
*Assistant Examiner* — Kristina M Hellman
(74) *Attorney, Agent, or Firm* — Morse, Barnes-Brown & Pendleton, P.C.; Martin Z. Zhang; Russell L. Widom

(57) ABSTRACT

The present invention relates to the treatment of sensory neuropathy induced by a marine neurotoxic poisoning. The invention further encompasses an in vitro method for producing a neuro-cutaneous model allowing to study the cellular and/or molecular mechanisms involved in said neuropathy, a neuro-cutaneous model obtainable according to said method, and applications thereof.

17 Claims, 15 Drawing Sheets
Specification includes a Sequence Listing.

Figure 4:
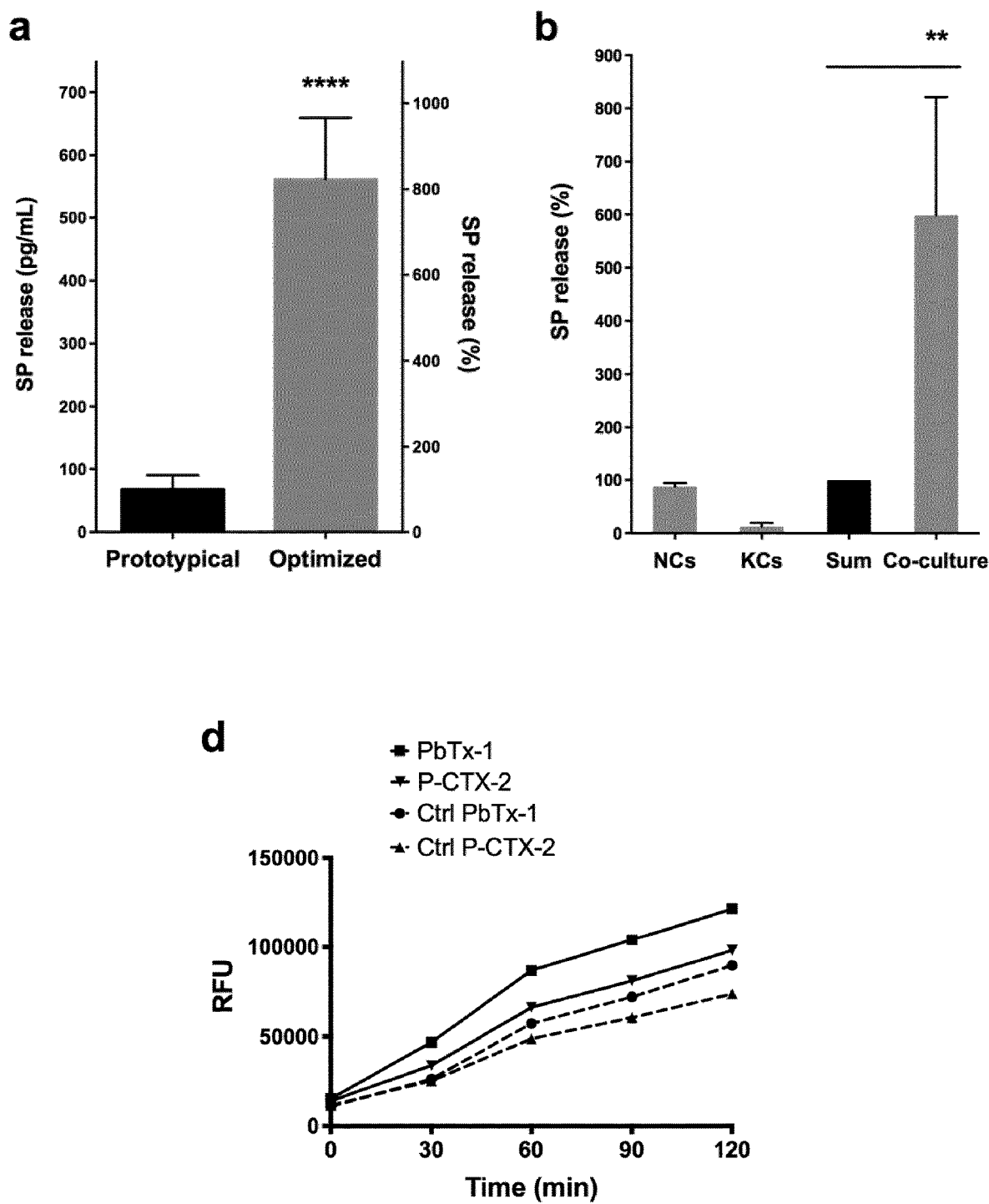

FIGURE 4 (continued)

SEQUENCE LISTING

<160> NUMBER OF SEQ ID NOS: 14

<210> SEQ ID NO 1
<211> LENGTH: 18
<212> TYPE: PRT
<213> ORGANISM: Artificial Sequence
<220> FEATURE:
<223> OTHER INFORMATION: PAR-2 inhibitor pepducin
<220> FEATURE:
<221> NAME/KEY: MISC_FEATURE
<222> LOCATION: (1)..(1)
<223> OTHER INFORMATION: N-palmitoyl
<220> FEATURE:
<221> NAME/KEY: MISC_FEATURE
<222> LOCATION: (18)..(18)
<223> OTHER INFORMATION: amino

<400> SEQUENCE: 1

Arg Ser Ser Ala Met Asp Glu Asn Ser Glu Lys Lys Arg Lys Ser Ala
1               5                   10                  15

Ile Lys

<210> SEQ ID NO 2
<211> LENGTH: 14
<212> TYPE: PRT
<213> ORGANISM: Artificial Sequence
<220> FEATURE:
<223> OTHER INFORMATION: PAR-2 inhibitor pepducin
<220> FEATURE:
<221> NAME/KEY: MISC_FEATURE
<222> LOCATION: (1)..(1)
<223> OTHER INFORMATION: N-palmitoyl
<220> FEATURE:
<221> NAME/KEY: MISC_FEATURE
<222> LOCATION: (14)..(14)
<223> OTHER INFORMATION: amino

<400> SEQUENCE: 2

Gly Asp Glu Asn Ser Glu Lys Lys Arg Lys Gln Ala Ile Lys
1               5                   10

<210> SEQ ID NO 3
<211> LENGTH: 21
<212> TYPE: PRT
<213> ORGANISM: Artificial Sequence
<220> FEATURE:
<223> OTHER INFORMATION: PAR-2 inhibitor pepducin
<220> FEATURE:
<221> NAME/KEY: MISC_FEATURE
<222> LOCATION: (1)..(1)
<223> OTHER INFORMATION: N-palmitoyl
<220> FEATURE:
<221> NAME/KEY: MISC_FEATURE
<222> LOCATION: (21)..(21)
<223> OTHER INFORMATION: amino

<400> SEQUENCE: 3

Arg Met Leu Arg Ser Ser Ala Met Asp Glu Asn Ser Glu Lys Lys Arg
1               5                   10                  15

Lys Arg Ala Ile Lys
            20

<210> SEQ ID NO 4
<211> LENGTH: 6
<212> TYPE: PRT
<213> ORGANISM: Artificial Sequence
<220> FEATURE:
<223> OTHER INFORMATION: PAR2 inhibitor peptide
<220> FEATURE:
<221> NAME/KEY: MISC_FEATURE

```
<222> LOCATION: (6)..(6)
<223> OTHER INFORMATION: amino

<400> SEQUENCE: 4

Phe Ser Leu Leu Arg Tyr
1               5

<210> SEQ ID NO 5
<211> LENGTH: 6
<212> TYPE: PRT
<213> ORGANISM: Artificial Sequence
<220> FEATURE:
<223> OTHER INFORMATION: PAR-2 inhibitor peptide
<220> FEATURE:
<221> NAME/KEY: MISC_FEATURE
<222> LOCATION: (6)..(6)
<223> OTHER INFORMATION: amino

<400> SEQUENCE: 5

Leu Ser Ile Gly Arg Leu
1               5

<210> SEQ ID NO 6
<211> LENGTH: 6
<212> TYPE: PRT
<213> ORGANISM: Artificial Sequence
<220> FEATURE:
<223> OTHER INFORMATION: PAR-2 inhibitor peptide

<400> SEQUENCE: 6

Ser Leu Ala Gly Lys Val
1               5

<210> SEQ ID NO 7
<211> LENGTH: 5
<212> TYPE: PRT
<213> ORGANISM: Artificial Sequence
<220> FEATURE:
<223> OTHER INFORMATION: PAR-2 inhibitor peptide
<220> FEATURE:
<221> NAME/KEY: MISC_FEATURE
<222> LOCATION: (1)..(1)
<223> OTHER INFORMATION: 2-aminothiazol-4-yl
<220> FEATURE:
<221> NAME/KEY: MISC_FEATURE
<222> LOCATION: (5)..(5)
<223> OTHER INFORMATION: amino

<400> SEQUENCE: 7

Leu Ile Gly Arg Leu
1               5

<210> SEQ ID NO 8
<211> LENGTH: 8
<212> TYPE: PRT
<213> ORGANISM: Artificial Sequence
<220> FEATURE:
<223> OTHER INFORMATION: PAR-2 inhibitor peptide

<400> SEQUENCE: 8

Ser His Asp Phe Arg Asp His Ala
1               5

<210> SEQ ID NO 9
<211> LENGTH: 6
<212> TYPE: PRT
<213> ORGANISM: Artificial Sequence
<220> FEATURE:
<223> OTHER INFORMATION: PAR-2 inhibitor peptide
```

```
<220> FEATURE:
<221> NAME/KEY: MISC_FEATURE
<222> LOCATION: (1)..(1)
<223> OTHER INFORMATION: acetyl
<220> FEATURE:
<221> NAME/KEY: MISC_FEATURE
<222> LOCATION: (6)..(6)
<223> OTHER INFORMATION: amino

<400> SEQUENCE: 9

Phe Phe Trp Phe His Val
1               5

<210> SEQ ID NO 10
<211> LENGTH: 8
<212> TYPE: PRT
<213> ORGANISM: Artificial Sequence
<220> FEATURE:
<223> OTHER INFORMATION: PAR-2 inhibitor peptide
<220> FEATURE:
<221> NAME/KEY: MISC_FEATURE
<222> LOCATION: (8)..(8)
<223> OTHER INFORMATION: amino

<400> SEQUENCE: 10

Arg Arg Phe Ser Leu Leu Arg Tyr
1               5

<210> SEQ ID NO 11
<211> LENGTH: 21
<212> TYPE: DNA
<213> ORGANISM: Artificial Sequence
<220> FEATURE:
<223> OTHER INFORMATION: PAR-2 inhibitor siRNA
<220> FEATURE:
<221> NAME/KEY: RNA
<222> LOCATION: (1)..(19)
<220> FEATURE:
<221> NAME/KEY: DNA
<222> LOCATION: (20)..(21)

<400> SEQUENCE: 11
uuaaacaggu uccacaucct a                                                   21

<210> SEQ ID NO 12
<211> LENGTH: 6
<212> TYPE: PRT
<213> ORGANISM: Artificial Sequence
<220> FEATURE:
<223> OTHER INFORMATION: PAR-2 cleavage peptide

<400> SEQUENCE: 12

Lys Val Asp Gly Thr Ser
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic peptide

<400> SEQUENCE: 13

Ser Leu Ile Gly Arg Leu
1               5

<210> SEQ ID NO 14
<211> LENGTH: 6
<212> TYPE: PRT
```

```
<213> ORGANISM: Artificial Sequence
<220> FEATURE:
<223> OTHER INFORMATION: Synthetic peptide

<400> SEQUENCE: 14

Ser Leu Ile Gly Lys Val
1               5
```

PROTEASE-ACTIVATED RECEPTOR-2 INHIBITORS FOR THE TREATMENT OF SENSORY NEUROPATHY INDUCED BY A MARINE NEUROTOXIC POISONING

CROSS REFERENCE TO RELATED APPLICATIONS

This patent application is the national stage of International Patent Application No. PCT/EP2020/059698, filed on Apr. 5, 2020, which claims the benefit and priority of European Patent Application No. 19305453.3, filed on Apr. 5, 2019, the disclosures being incorporated by reference herein in their entirety as part of the present application.

INTRODUCTION

The present invention relates to the treatment of sensory neuropathy induced by a marine neurotoxic poisoning. The invention further encompasses an in vitro method for producing a neuro-cutaneous model allowing to study the cellular and/or molecular mechanisms involved in said neuropathy, a neuro-cutaneous model obtainable according to said method, and applications thereof.

Ciguatoxins (CTXs) and brevetoxins (PbTxs) are phycotoxins that can accumulate along the marine food chain and thus cause seafood poisoning in humans, namely "Ciguatera Fish Poisoning" (CFP) and "Neurotoxic Shellfish Poisoning" (NSP), respectively (Friedman et al. 2017, Dechraoui et al. 1999). CFP is characterized by early gastrointestinal symptoms and typical sensory disorders, and, in the worst cases, cardiovascular and central neurological troubles can also appear. NSP is considered a mild form of CFP with similar but less severe symptoms. The most distressing symptoms of these intoxications are sensory disorders, which typically consist of perioral and acral paresthesia, painful sensations on contact with mild cold (cold dysesthesia) and intense pruritus without visible lesions (Bagnis and Legrand 1987, Calvert et al. 1987, Derouiche et al. 2000, Chateau-Degat et al. 2007). Other painful sensations can include headaches, myalgia, dental pain and/or arthralgia. These sensory symptoms and their persistence, which can last for several weeks or even months or years in the case of CFP, are strongly suggestive of a neuropathic disease (Cameron and Capra 1993, Derouiche et al. 2000, Pearn 2001, Schnorf et al. 2002, Isbister and Kiernan 2005).

Ciguatoxins and brevetoxins are structural and functional analogs, which bind to a common site (named neurotoxin binding site 5) located on voltage-gated sodium channels (VGSCs), albeit with variable affinity. Mechanistically, it is well established that CTX- or PbTx-induced disturbances are primarily mainly due to the activation of voltage-gated sodium channels in the nervous system, which, together with an inhibition of voltage-gated potassium channels, can lead to an increase in neuronal excitability. In addition to their action on the nervous system, CTXs and PbTxs are also shown to exert effects on the immune system.

However, little is known about the pathophysiology of syndromes induced by CTX or PbTx exposure, such as sensory neuropathy, or a potential individual susceptibility to long lasting effects of CFP/NSP. Thus, the current knowledge does not allow the specific treatment of these neurotoxic marine poisonings. Current therapies (such as lidocaine, antidepressants, antiepileptic, etc.) are essentially palliative, directed to symptoms, and non-specific. Among the recommended treatments, notably for CFP, hyperosmotic mannitol used in intravenous infusion is most often cited since its success on intoxicated patients who recovered spectacularly. The effectiveness of this treatment is supposed to be based on a restoration of the ionic and osmotic balance disturbed by ciguatoxins and brevetoxins in neurons and Schwann cells. Several case reports and an open clinical trial have shown its effectiveness in severe cases of poisoning supported early. However, studies in animal models and a double-blind clinical trial on non-severe forms of intoxication concluded that mannitol was not effective. In addition, its intravenous administration, which requires hospitalization, does not allow its use as an outpatient.

There is thus still a need for a treatment of marine neurotoxic poisoning, more particularly mediated by sodium channel-activating neurotoxins, which efficiently alleviates, cures or even prevents one or more of the disorders associated therewith, especially sensory neuropathy.

There is also a need to identify new tools for medical research and drug screening, to identify treatment of these disorders.

The present invention addresses the above discussed need in the art.

The Inventors have indeed developed a coculture model of sensory neurons and keratinocytes which can be positioned as a relevant in vitro tool for exploring cellular and molecular processes involved in the genesis of sensory neuropathy induced by exposure to marine sodium channel-activating neurotoxins. In addition to demonstrating a striking synergistic role of keratinocytes in the substance P release induced by such exposure in this coculture model, the present results reveal that these neurotoxins induce a marked calcium response in epidermal keratinocytes, thus highlighting these non-excitable cells as potential cellular targets for these toxins.

Moreover, the Inventors have surprisingly discovered that, in both sensory neurons and keratinocytes, the Nav-dependent calcium signal triggered by these marine neurotoxins involved the activation of protease activated receptor-2 (PAR-2), and that cathepsin S is a molecular mediator involved in this PAR-2 activation. These results pave the way for specific treatments of sensory disturbances induced by poisoning with marine sodium channel-activating neurotoxins such as ciguatoxins and brevetoxins, which rely on direct or indirect PAR-2 inhibitors, in particular cathepsin S inhibitors.

SUMMARY OF THE INVENTION

In a first aspect, the invention relates to a protease-activated receptor-2 (PAR-2) inhibitor for use in treating a sensory neuropathy induced by poisoning with a marine sodium channel-activating neurotoxin in a subject.

In a preferred embodiment, the sensory neuropathy is pruritus, paresthesia, dysesthesia, allodynia, myalgia, arthralgia, dysuria, dental pain, or any combinations thereof.

In a preferred embodiment, the sensory neuropathy is mediated via the activation of voltage-gated sodium channels (VGSCs) by the marine neurotoxin.

In a preferred embodiment, the marine neurotoxin binds to the alpha subunit of voltage-dependent sodium channels, preferably to the neurotoxin binding site 5 of said alpha subunit.

In a preferred embodiment, the marine neurotoxin comprises a ciguatoxin (CTX), a brevetoxin (PbTx), an active metabolite thereof, or any combinations thereof.

In a preferred embodiment, the protease-activated receptor-2 (PAR-2) inhibitor is a PAR-2 full antagonist or a PAR-2 biased antagonist, preferably a PAR-2 full antagonist.

In a preferred embodiment, the protease-activated receptor-2 (PAR-2) inhibitor for use is a small molecule, a peptide such as a pepducin, a polypeptide such as an antibody, a polynucleotide such as RNAi or an aptamer, or any combinations thereof.

In a preferred embodiment, the protease-activated receptor-2 (PAR-2) inhibitor for use is GB83 or GB88, or a derivative thereof.

In a preferred embodiment, the protease-activated receptor-2 (PAR-2) inhibitor for use inhibits Cathepsin-S-mediated PAR-2 signaling.

In a preferred embodiment, the protease-activated receptor-2 (PAR-2) inhibitor for use is the Cathepsin S inhibitor Cbz-Phe-Leu-COCHO, or a derivative thereof.

In a preferred embodiment, the protease-activated receptor-2 (PAR-2) inhibitor for use is comprised in a pharmaceutical composition.

In another aspect, the invention is directed to an in vitro method for producing a neuro-cutaneous model capable of releasing sensory neuropeptides, said method comprising:
 a) growing a population of sensory neurons in a culture medium suitable for neurites formation;
 b) growing a population of keratinocytes with the population of sensory neurons grown in step a) in a culture medium suitable for keratinocytes adherence; and
 c) growing the co-population of keratinocytes and sensory neurons obtained in step b) in a culture medium suitable for keratinocytes differentiation.

In a preferred embodiment, the culture medium of step a) and the one of step c) comprise extracellular calcium, preferably at a physiological concentration; and/or the culture medium of step b) does not comprise extracellular calcium or comprises extracellular calcium below a physiological concentration.

In a preferred embodiment, the culture medium of step a), and optionally the one of step c), comprise(s) at least one neurotrophic agent, such as any one of B27, nerve growth factor (NGF), brain-derived neurotrophic factor (BDNF) or any combinations thereof; and/or the culture medium of step b) comprises at least one epidermal growth agent, such as epidermal growth factor (EGF).

In a further aspect, the invention pertains to an in vitro neuro-cutaneous model obtainable according to the in vitro method for producing a neuro-cutaneous model according to the invention.

In a last aspect, the invention relates to an in vitro screening method for identifying an agent or combination of agents useful in treating a sensory neuropathy induced by poisoning with a marine sodium channel-activating neurotoxin, said method comprising:
 contacting the in vitro neuro-cutaneous model according to the invention, with a candidate agent or a combination of candidate agents;
 wherein the detection of PAR-2 inhibition or Cathepsin S inhibition or neuropeptide release inhibition in said model is indicative that said agent or combination of agents is useful in treating a sensory neuropathy induced by poisoning with a marine sodium-channel-activating neurotoxin.

LEGENDS TO THE FIGURES

Figure 1:
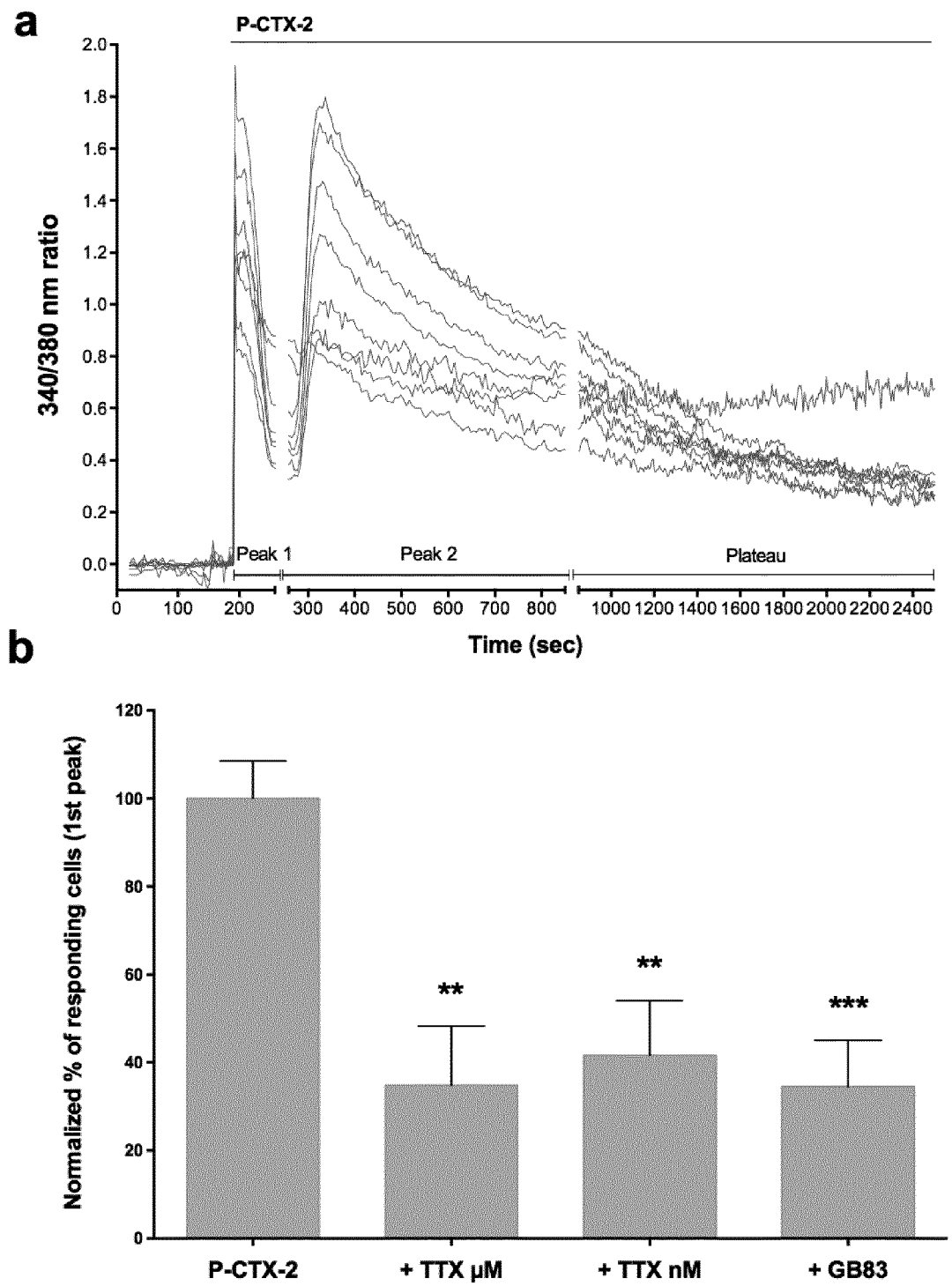
Figure 1:
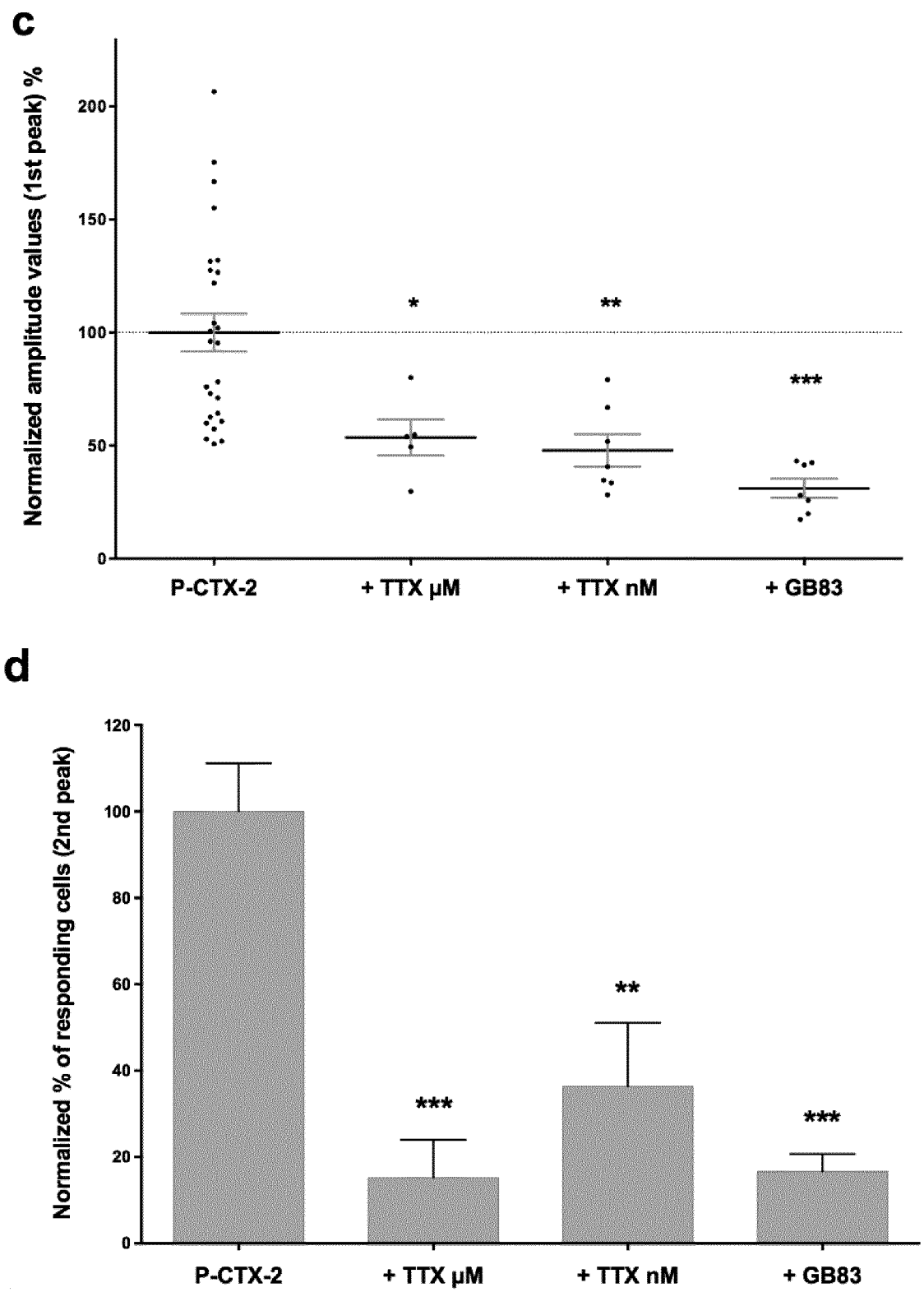
Figure 1:
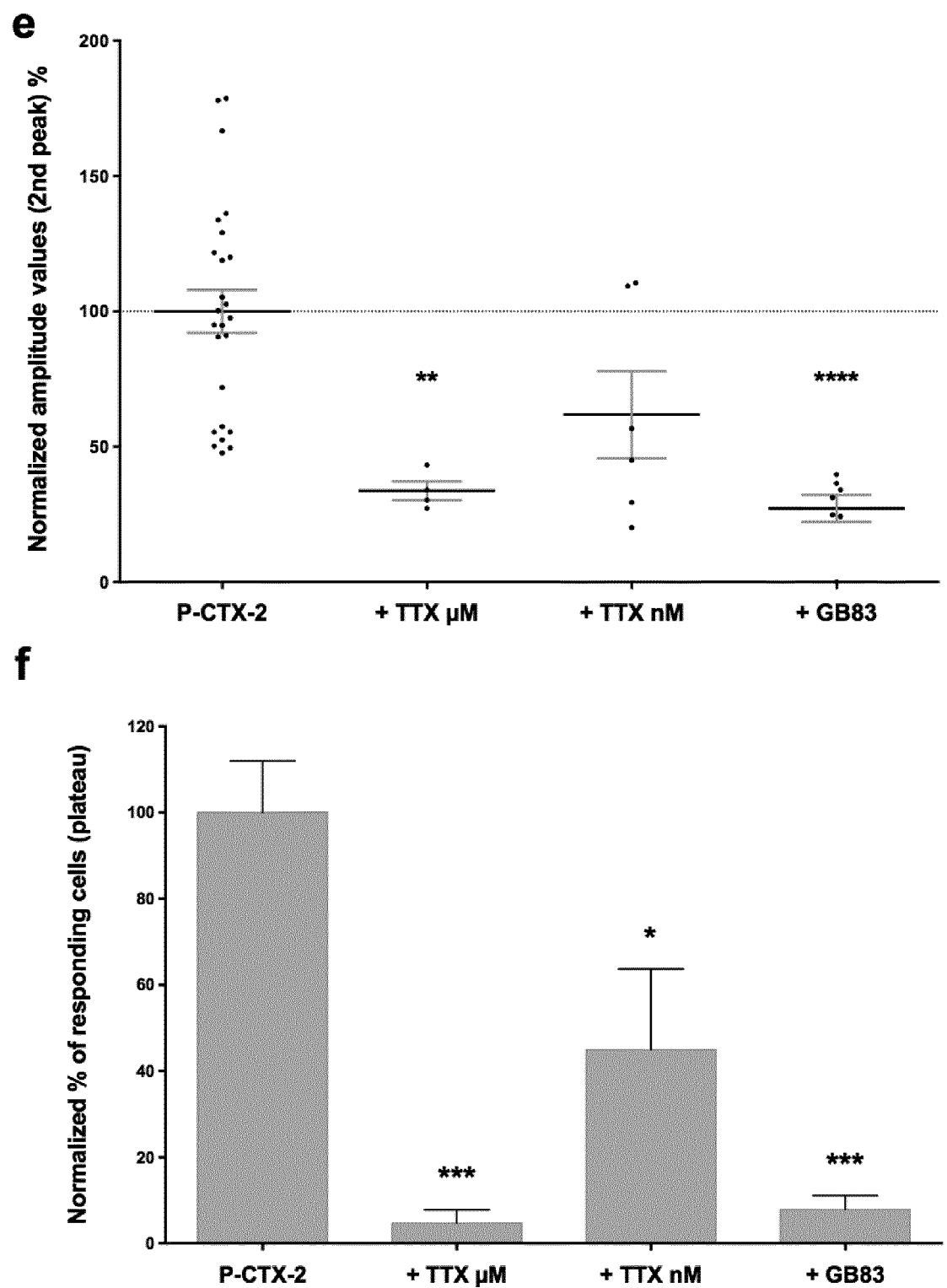
Figure 1:
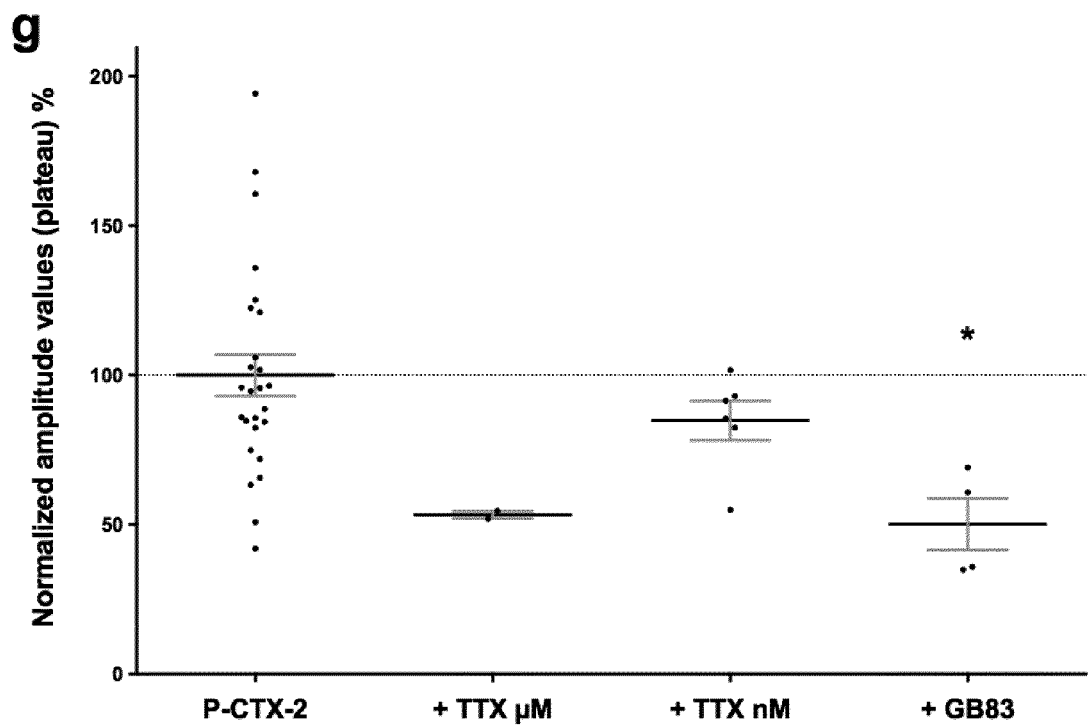

FIG. 1. In DRG neurons, P-CTX-2-evoked calcium response is mediated by TTX-s, TTX-r $Na_v$ channels and PAR-2 receptor. (a) Representative patterns of calcium signal responses evoked by P-CTX-2 (10 nM) in DRG neurons. Calcium response was decomposed into the following 3 phases: 1) a first immediate acute $[Ca^{2+}]_i$ increase named the "first peak", followed by 2) a second $[Ca^{2+}]_i$ increase called the "second peak", which ended with 3) a long-lasting calcium "plateau", which almost never returned to the baseline level. Vehicle control (MeOH 0.05%) had no effect on $[Ca^{2+}]_i$ (data not shown). Normalized percentages of responding cells and amplitude values in still responding cells recorded during the first peak (b and c, respectively), the second peak (d, e), or the plateau (f, g) of the calcium signal in response to 10 nM P-CTX-2 alone (control condition, n=26) or following pretreatment with 100 μM TTX (n=6), 300 nM TTX (n=8) and 5 μM GB83 (n=7) expressed as the mean±standard error of the mean (SEM). n represents the number of experiments in which 40 to 100 neuronal cells were included in the analysis. The data were statistically analyzed using a one-way ANOVA, followed by Dunnett's post hoc test for multiple comparisons. *$P<0.05$, $P<0.01$, *$P<0.001$, ****$P<0.0001$.

Figure 2:
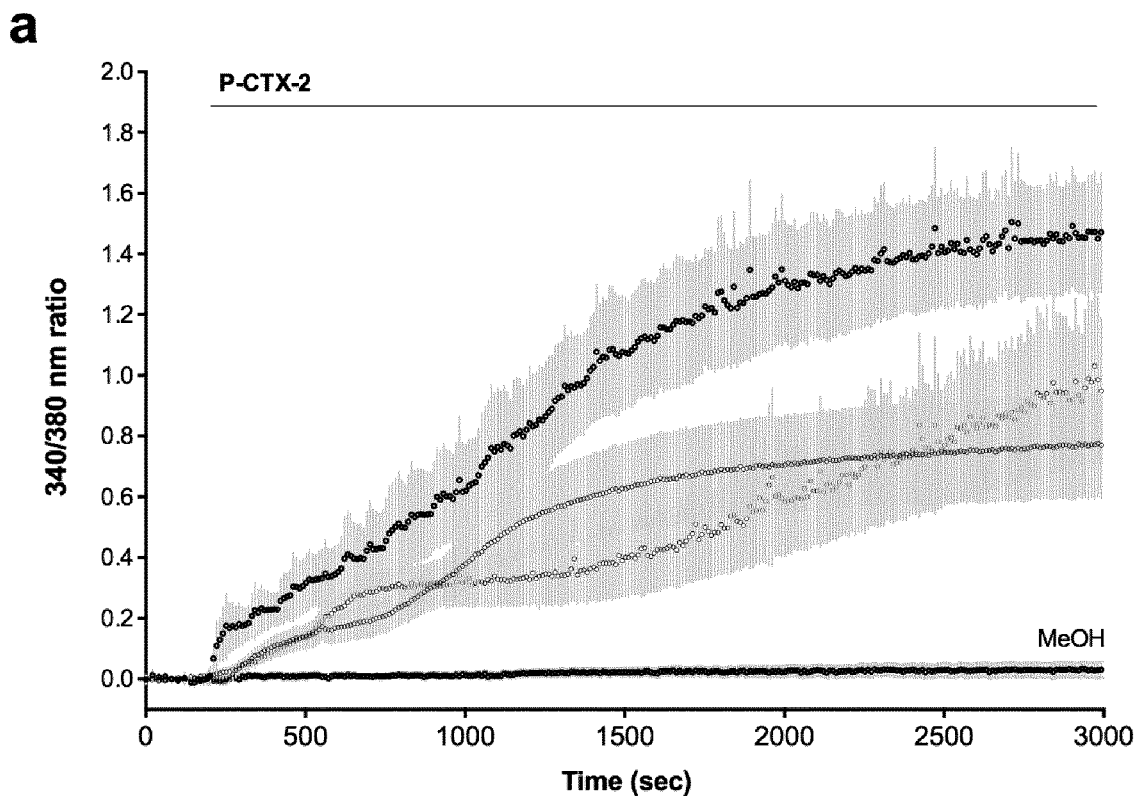
Figure 2:
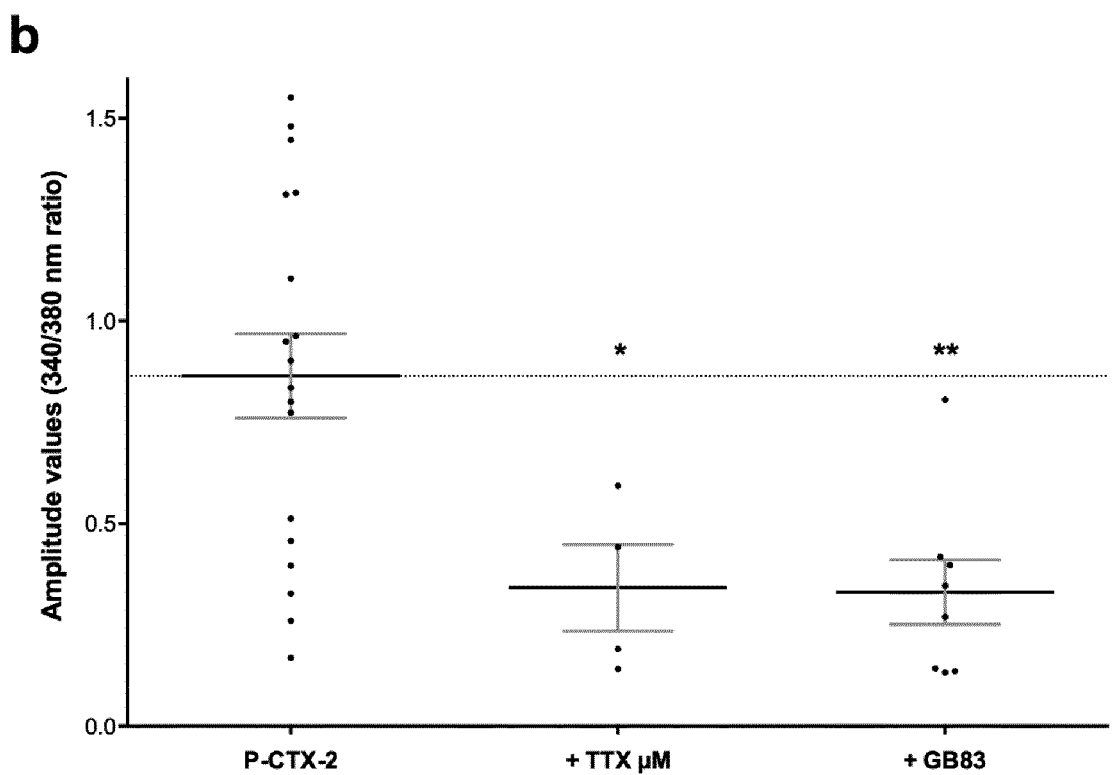

FIG. 2. In human primary keratinocytes, P-CTX-2 directly induced a calcium response mediated by $Na_v$ channels and PAR-2. (a) Representative patterns of calcium signal responses evoked by P-CTX-2 (10 nM) in keratinocytes obtained from 3 different patients (n=101, 64, and 18 cells). The bottom curve represents the values obtained with the vehicle control (MeOH 0.05%) in keratinocytes from one patient. Outlines represent the average calcium response of all analyzed cells±SEM. (b) Average amplitude values of the calcium signal obtained in all analyzed keratinocytes 45 min following exposure to 10 nM P-CTX-2 (n=18) with or without pretreatment with 100 μM TTX (n=4) or 50 μM GB83 (n=8) 5 min before the P-CTX-2 application, where n is the number of experiments in which 30 to 100 keratinocytes were analyzed. Statistical analysis was conducted using an ordinary one-way ANOVA, followed by Dunnett's post hoc test. *$P<0.05$, **$P<0.01$.

Figure 3:
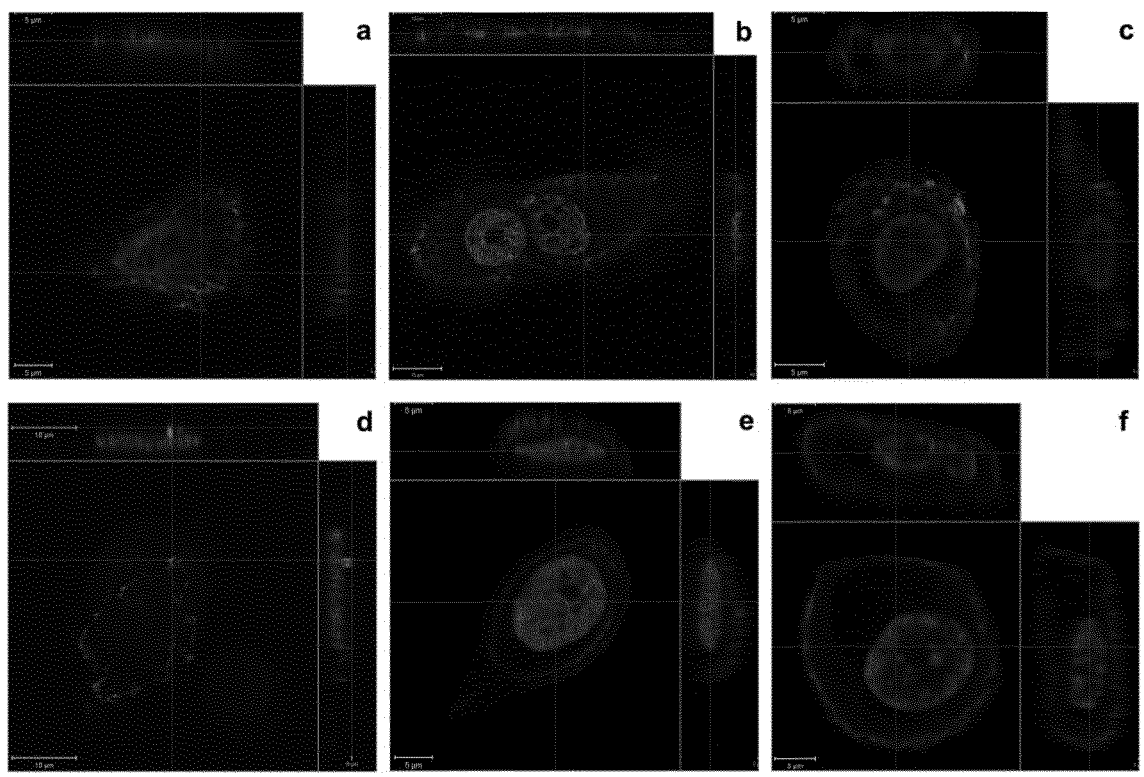

FIG. 3. In human keratinocytes, the $Na_v$-activating toxins P-CTX-2 and PbTx-1 induce PAR-2 internalization. Confocal laser-scanning micrographs of primary human epidermal keratinocytes following exposure to 10 nM P-CTX-2 (a), 1 μM PbTx-1 (b), 500 nM trypsin (as a positive control (c), or their vehicle controls, i.e., MeOH 0.05%, MeOH 0.1% or HCl 1 mM 0.05%, respectively (d, e and f), for 45 min at 37° C. After the treatment, the cells were fixed and immunolabelled before confocal imaging to localize PAR-2 as described in the Materials and Methods.

FIG. 4. Keratinocytes, TTX-s, TTX-r Nav, PAR-2 and Cat-S are major cellular and molecular players in P-CTX-2-induced SP release in the co-culture. (a) Optimization of the co-culture model. P-CTX-2-induced SP levels (expressed in pg/mL and as normalized values) released in the old (n=4) versus new (n=19) co-culture model were statistically analyzed using an unpaired t-test, followed by Welch's correction (two-tailed P value). (b) Synergistic effect of keratinocytes on SP release in the co-culture. The sum of the SP levels released in independent DRG neuron and keratinocyte monocultures (NCs and KCs, respectively) following P-CTX-2 exposure was compared to the P-CTX-2-induced SP levels released in the co-culture. Normalized values obtained from n=10 experiments were statistically analyzed using a Wilcoxon test for paired data (two-tailed P value). (c) Effect of selected antagonists on the P-CTX-2-evoked SP release in the co-culture. Normalized SP levels after P-CTX-2 exposure without (n=23) or with pretreatment with 100 μM TTX (n=13), 300 nM TTX (n=4), 5 μM GB83 (n=9), 10 μM E64 (n=4) or 10 nM Z-FL-COCHO (n=4) were statistically analyzed using multiple comparison one-way ANOVA with Dunnett's post hoc test. P-CTX-2 (10 nM) was applied for 90 min with or without pre-treatment with pharmacological antagonists. The SP levels were measured in the supernatants by an EIA assay. The values obtained under the vehicle control conditions (MeOH 0.05%) were subtracted from those obtained under the 10 nM P-CTX-2 conditions, and then, the average SP levels in pg/mL were normalized. The normalized values are expressed as the mean±SEM, and n is the number of experiments. (d) Representative time course curves of Cat-S activity measured in supernatants from co-cultures treated for 90 min with 10 nM P-CTX-2, 2 µM PbTx-1 or their vehicle controls (MeOH 0.05% or DMEM: DMEM/F12 1:1, respectively). (e) Reaction rate of Cat-S activity in supernatants from co-cultures treated with 2 µM PbTx-1 (n=5) or 10 nM P-CTX-2 (n=4) expressed as a percentage of the value obtained under the vehicle control condition and the mean±SEM. Statistical analysis was performed using a one-tailed paired t-test followed by Welch's correction post hoc test. *P<0.05, P<0.01, *P<0.001, ****P<0.0001.

Figure 5:
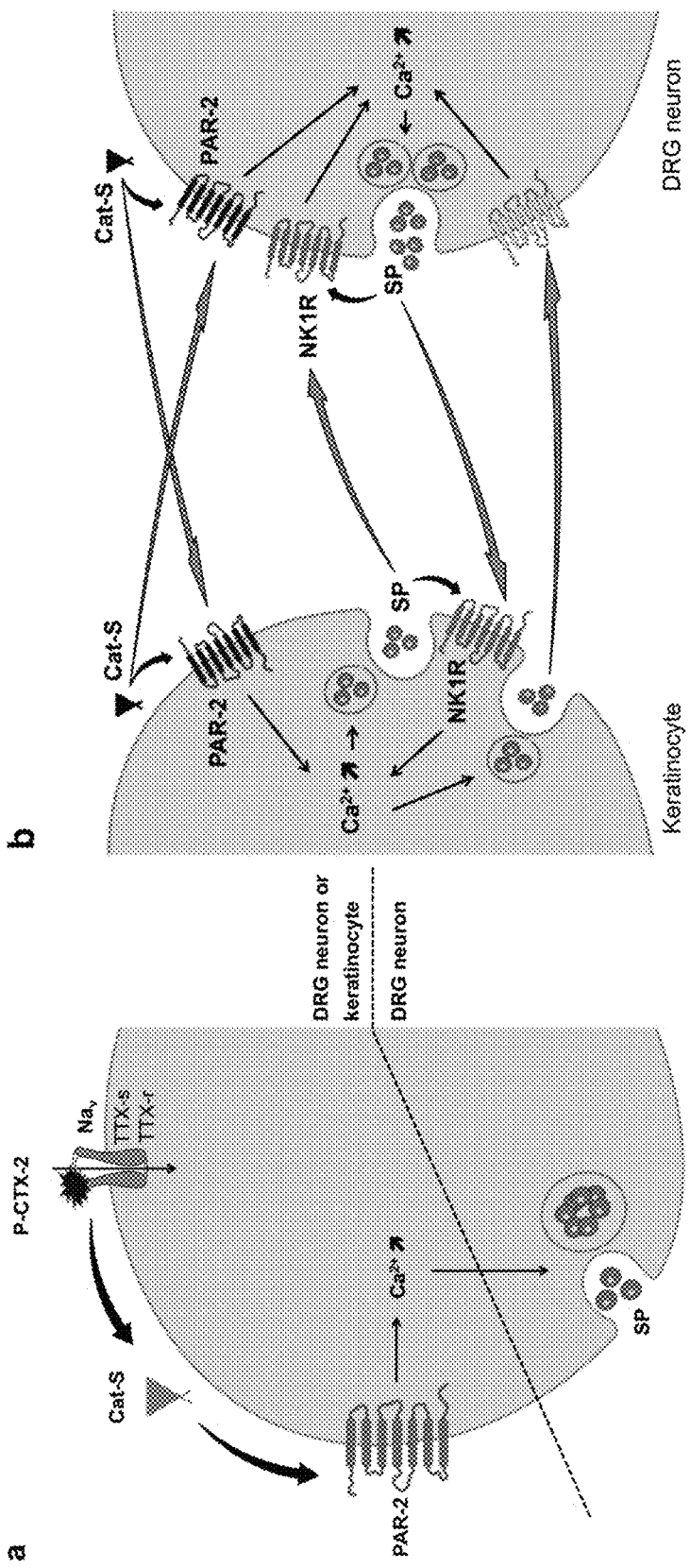

FIG. 5. Keratinocytes, Nay channels, Cat-S and PAR-2 are cellular and molecular effectors of the P-CTX-2-elicited SP release in the co-culture. (a) Newly identified molecular mechanisms driving P-CTX-2-induced SP release from co-cultured sensory neurons and keratinocytes. Nav activation by P-CTX-2 in DRG neuron cultures and keratinocytes triggers an increase in Cat-S activity which, through PAR-2 activation, promotes a subsequent increase in [Ca2+]i. In sensory neurons, this effect is sufficient to induce SP release. In DRG neuron cultures, Cat-S could stem from DRG neurons or glial cells. (b) Putative mediators, including Cat-S/PAR-2 and SP/NK1R, involved in the cross-talk between DRG neurons and keratinocytes (blue arrows) that leads to the synergistic role of keratinocytes in P-CTX-2-induced SP release in the co-culture. Following P-CTX-2 exposure, SP released from neurons could elicit SP release in keratinocytes through NK1R activation. Cat-S from DRG neurons (and/or Schwann cells) could activate PAR-2 expressed in keratinocytes. Vice versa, Cat-S from keratinocytes could activate the neuronal PAR-2, and mediators other than SP released from keratinocytes could also potentiate the P-CTX-2-induced SP release in sensory neurons.

Figure 6:
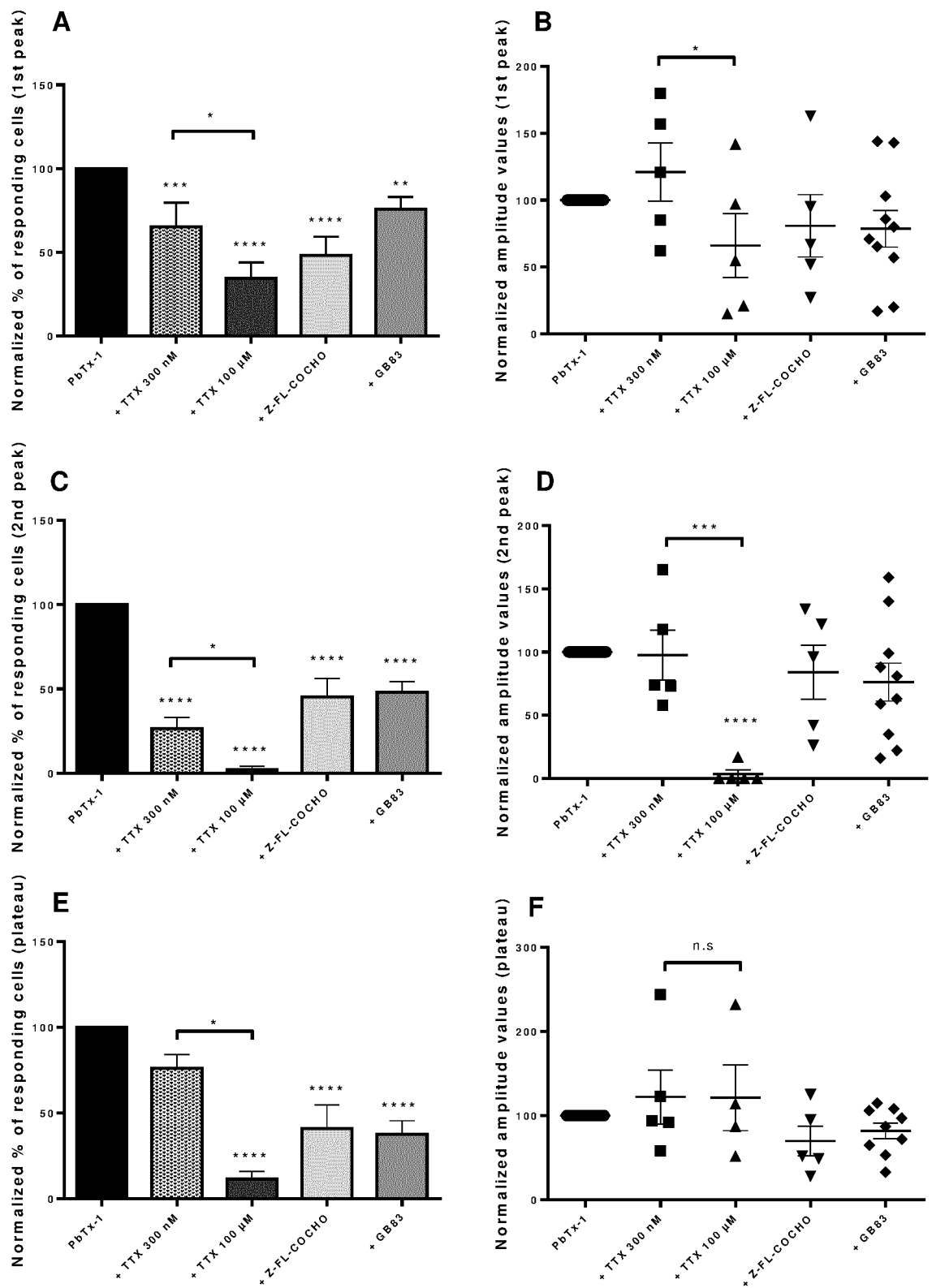

FIG. 6. Effects of different antagonists on PbTx-1-induced calcium response in sensory neurons. Both antagonists were pre-incubated 10 minutes before the injection of 1 µM of PbTx-1. Normalized percentages of responding cells and normalized amplitude values were recorded for the first peak, the second peak, or the plateau in response to 1 µM of PbTx-1 alone (control condition, n=15) or with pre-treatment with 300 nM of TTX (n=5), 100 µM of TTX (n=5), 10 nM of Z-FL-COCHO (n=9) and 5 µM of GB83 (n=9), expressed as the mean±SEM. n represents the number of experiments in which 50 to 100 neuronal cells have been integrated to the calcium analysis. Statistical analysis was performed with a one-way ANOVA for multiple comparisons between control and each condition, and between the pre-treatment with TTX 300 nM and the pre-treatment with TTX 100 µM followed by a Fisher's LSD test.*p<0.05, p<0.01, *p<0.001 and ****p<0.0001.

Figure 7:
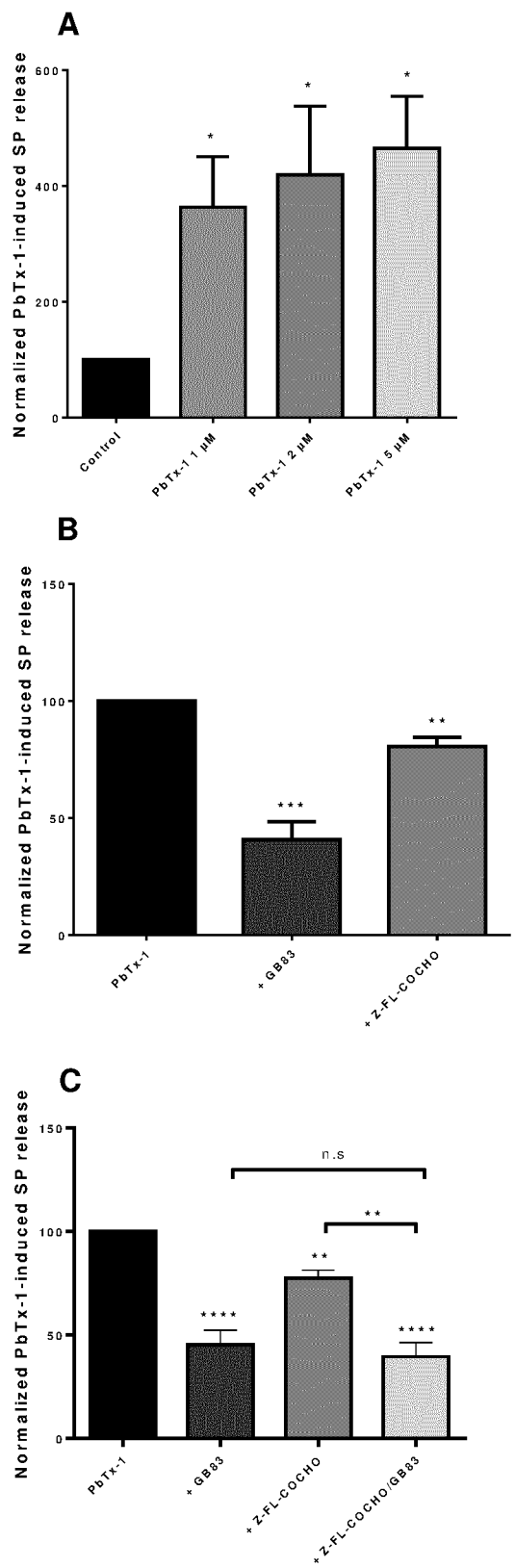

FIG. 7. Effects of GB83 and Z-FL-COCHO on the SP release induced by PbTx-1 from co-cultured sensory neurons and keratinocytes. (A) Co-cultures were treated for 90 minutes with different concentrations of PbTx-1 1 µM (n=4), 2 µM (n=6), 5 µM (n=5). Data were normalized according to the control condition. Data were expressed as mean±SEM and statistically analyzed with paired t-test between PbTx-1 condition versus control.*p<0.05. (B) Both antagonists were pre-incubated 10 minutes before 1 µM of PbTx-1 for 90 minutes. Normalized data were expressed as the mean±SEM of 7 experiments. Data were analyzed using one-way ANOVA followed by a Fisher's LSD test. *p<0.05, p<0.01 and *p<0.001. (C) Both antagonists were pre-incubated 10 min before 1 µM of PbTx-1 for 90 min. Data were expressed as the mean±SEM of 4 experiments. Data were statistically analyzed using one-way ANOVA for multiple comparisons to control, between GB83 alone and GB83/Z-FL-COCHO and between Z-FL-COCHO alone and GB83/Z-FL-COCHO followed by a Fisher's LSD test. *p<0.05, p<0.01, *p<0.001 and ****p<0.0001.

Figure 8:
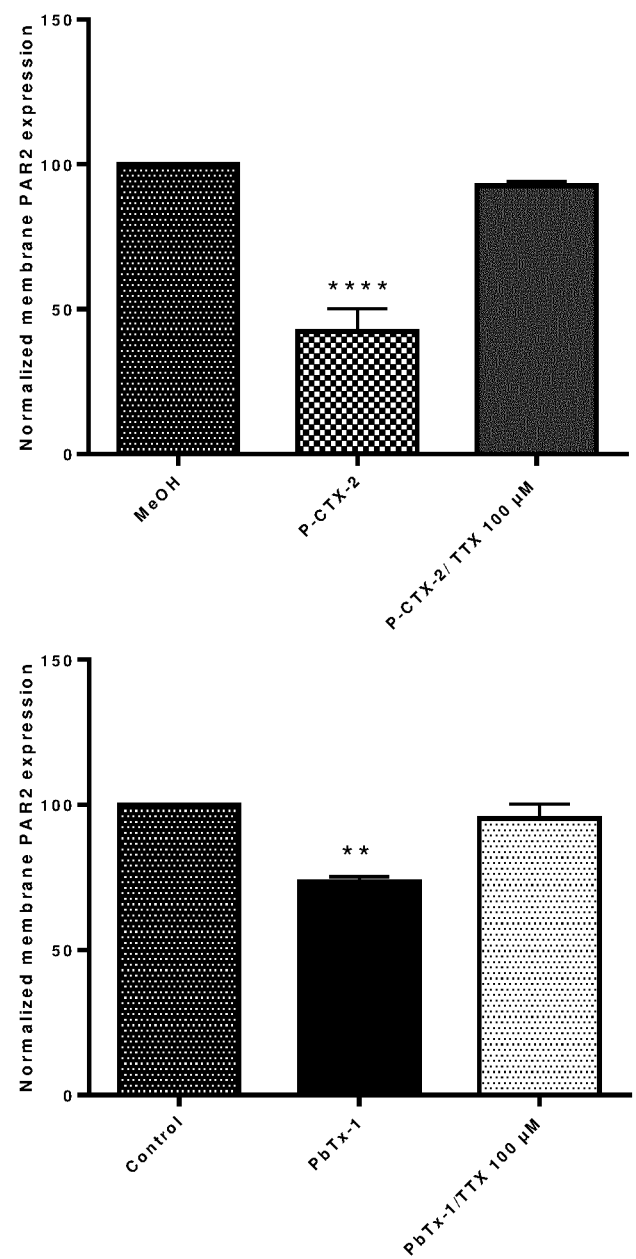

FIG. 8. Internalization of PAR-2 induced by the PbTx-1 and P-CTX-2 is Nav-dependent in sensory neurons. (A) Effects of 1 µM of PbTx-1 and 1 µM of PbTx-1 with pre-treatment of 100 µM of TTX on PAR-2 membrane expression in sensory neurons. Data were expressed as the mean±SEM of 3 experiments. Data were statistically analyzed using one-way ANOVA followed by a Fisher's LSD test for multiple comparisons for multiple comparisons to control. *p<0.05, p<0.01 and *p<0.001. (B) Effects of 10 nM of P-CTX-2, 10 nM of P-CTX-2 with pre-treatment 100 µM of TTX on PAR-2 membrane expression in sensory neurons. Data were expressed as the mean±SEM of 3 experiments. Data were statistically analyzed using one-way ANOVA followed a Fisher's LSD test for multiple comparisons. *p<0.05, p<0.01, *p<0.001 and ****p<0.0001.

Figure 9:
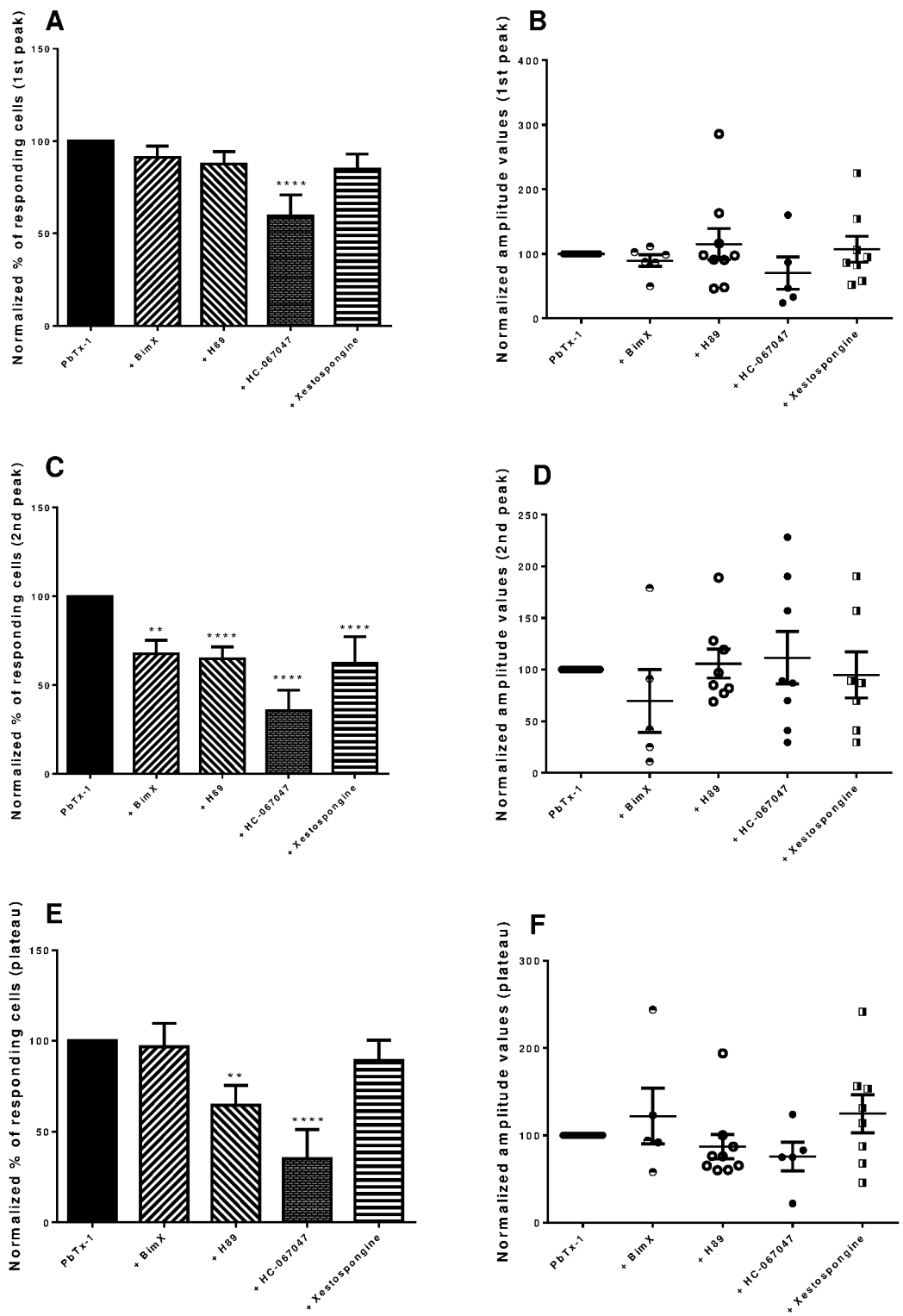

FIG. 9. Effects of different antagonists on PbTx-1-induced calcium response in sensory neurons. Antagonists were pre-incubated 10 minutes before 1 µM of PbTx-1. Normalized percentages of responding cells and associated amplitude values recorded for the first peak, the second peak, or the plateau in response to 1 µM of PbTx-1 alone (control condition, n=15) or with pre-treatment with 10 µM of BimX (n=6), 5 µM of H89 (n=9), 10 µM of HC-067047 (n=5), and 5 µM of Xestospongin C (n=8) were expressed as the mean±SEM. "n" represents the number of experiments in which 50 to 100 neuronal cells have been integrated to the calcium analysis. The statistical analysis was performed with one-way ANOVA for multiple comparisons to control followed by a Fisher's LSD test.*p<0.05, p<0.01, *p<0.001, ****p<0.0001.

Figure 10:
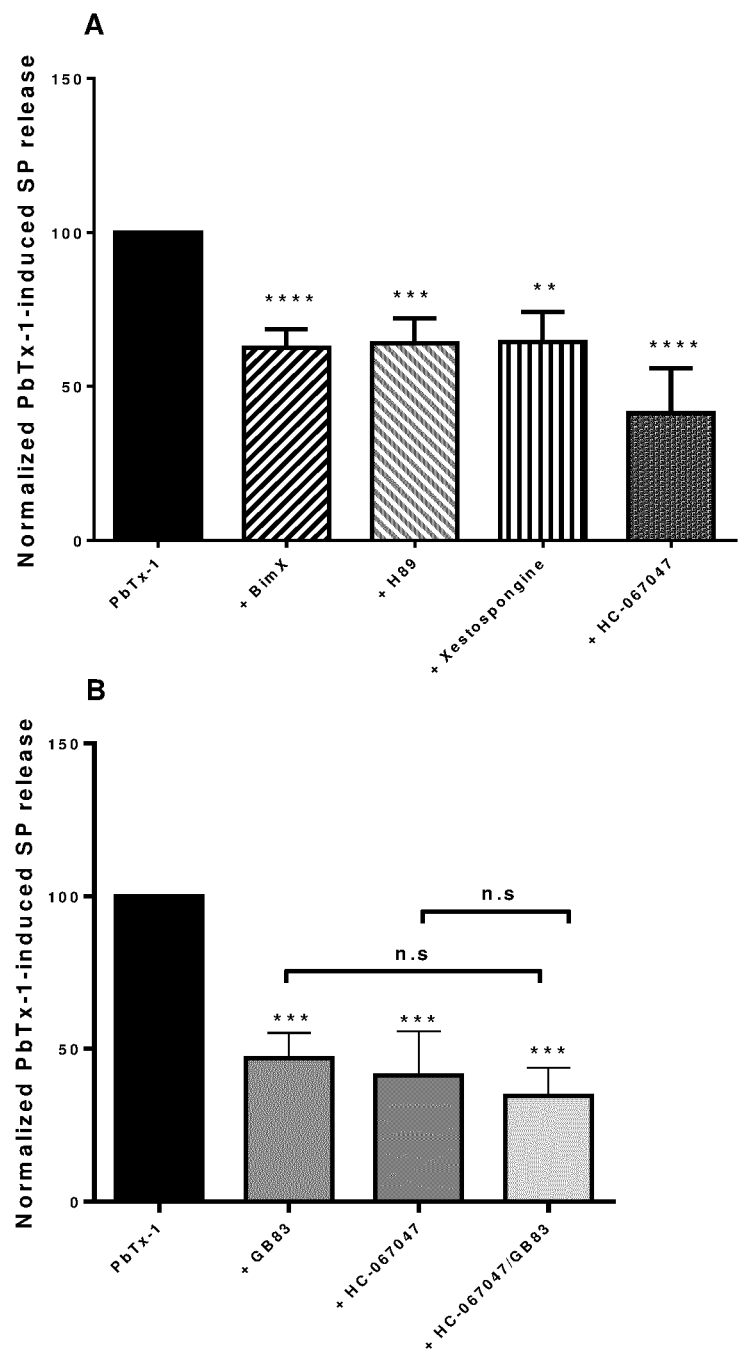

FIG. 10. Involvement of different actors of PAR-2 signaling in PbTx-1-induced SP release. Antagonists were pre-incubated 10 minutes before PbTx-1 1 µM treatment for 90 minutes. (A) Normalized levels of SP from supernatants of co-culture in response to 1 µM of PbTx-1 alone (control condition, n=7) or with pre-treatment with 10 µM of BimX (n=5), with 5 µM of H89 (n=5), with 10 µM of HC-067047 (n=3), with 5 µM of Xestospongin C (n=4) were expressed as the mean±SEM. The data were statistically analyzed using an one-way ANOVA for multiple comparisons to control followed by a Fisher's LSD test. *p<0.05, p<0.01, *p<0.001, ****p<0.0001. (B) Normalized levels of SP in supernatants of co-culture in response to PbTx-1 1 µM alone (control condition, n=3) or with pre-treatment with 5 µM of GB83 5 (n=3), with 10 µM of HC-067047 (n=3) or with GB83/HC-067047 (n=3) were expressed as the mean±SEM. The data were analyzed using one-way ANOVA for multiple comparisons and followed by a Fisher's LSD test. *p<0.05, p<0.01, *p<0.001, ****p<0.0001.

Figure 11:
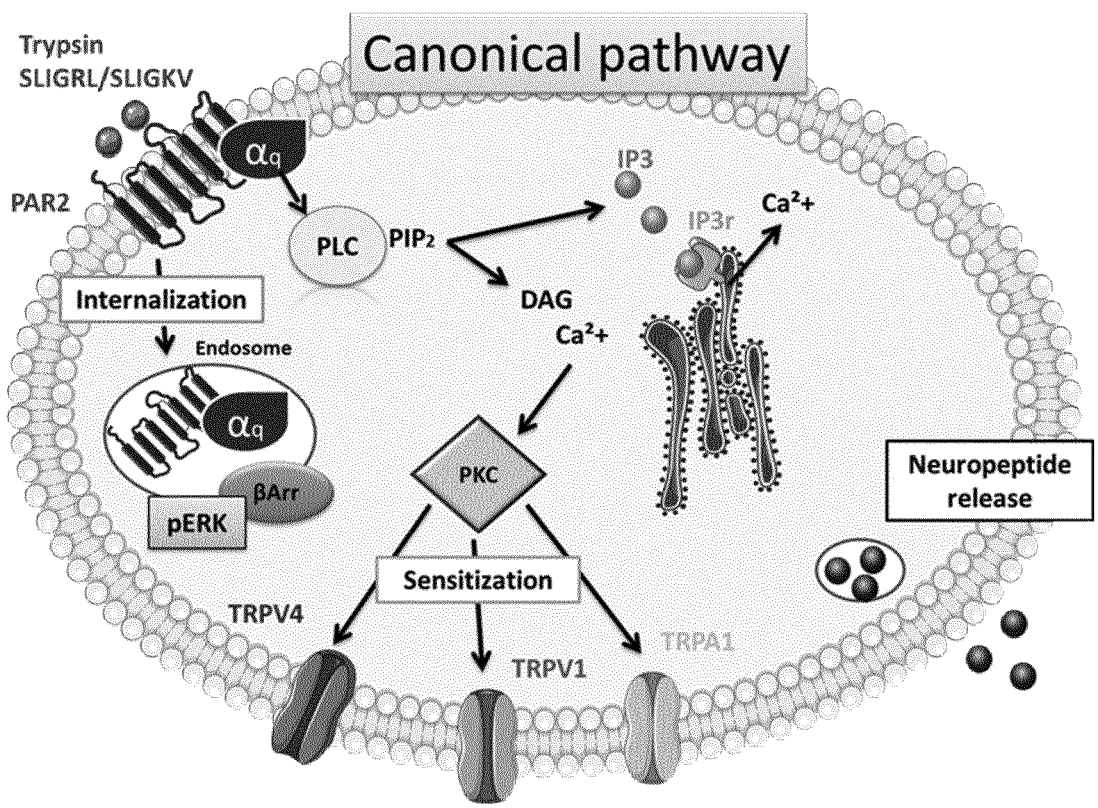

FIG. 11. Canonical pathway downstream of PAR-2: SLIGRL (SEQ ID NO: 13), SLIGKV (SEQ ID NO: 14).

Figure 12:
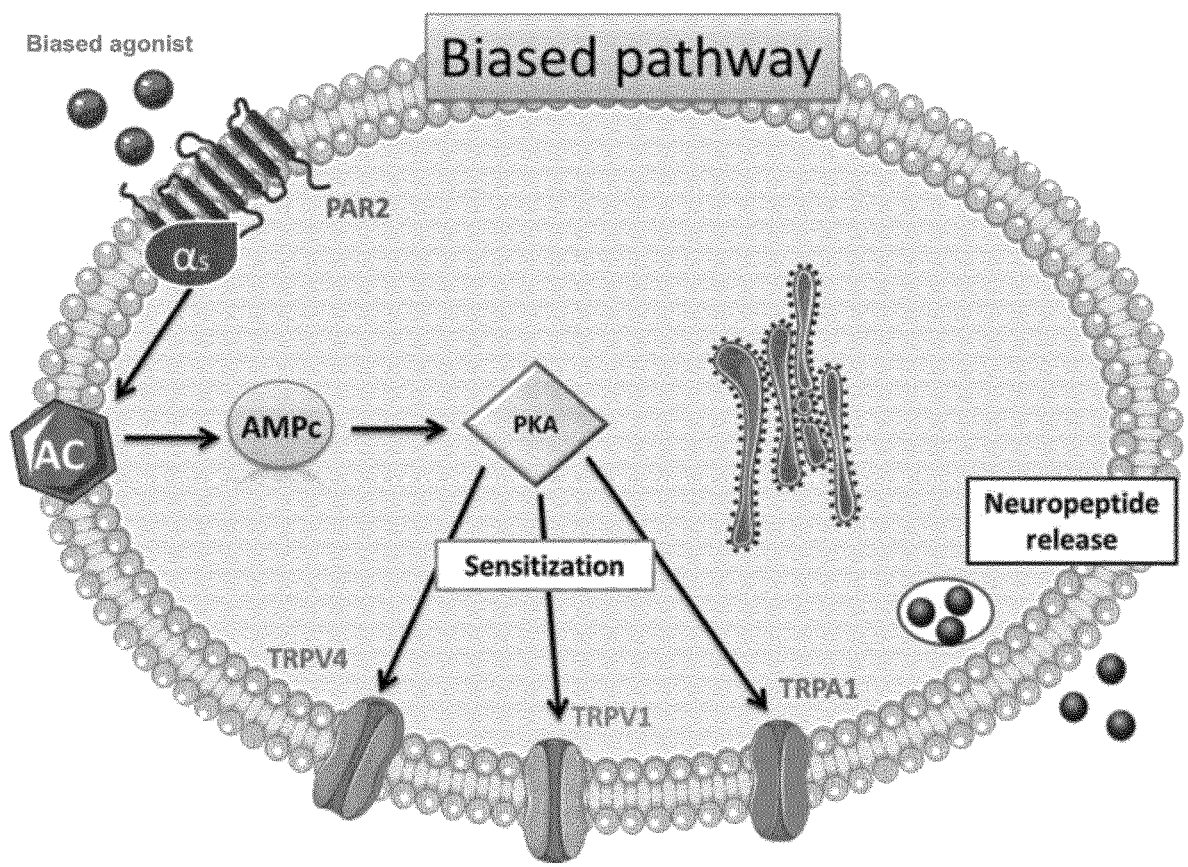

FIG. 12. Biased pathway downstream of PAR-2

DETAILED DESCRIPTION OF THE INVENTION

Unless otherwise defined herein, scientific and technical terms used in connection with the present invention shall have the meanings that are commonly understood by those of ordinary skill in the art. Further, unless otherwise required by context, nomenclatures used herein, and techniques of cell and tissue culture are those well-known and commonly used in the art.

The present invention may be understood more readily by reference to the following detailed description, included preferred embodiments of the invention, and examples included herein.

The Inventors have discovered that key features of exposure to marine sodium channel-activating neurotoxins, such as sensory neuropeptide release and/or increase in intracellular calcium in particular in sensory neurons and/or keratinocytes, can be completely abrogated by specific inhibition of protease-activated receptor-2 (PAR-2).

Accordingly, in a first aspect, the present invention relates to a protease-activated receptor-2 (PAR-2) inhibitor for use in treating a sensory neuropathy induced by poisoning with a marine sodium channel-activating neurotoxin in a subject.

In particular, the present invention is directed to the use of a protease-activated receptor-2 (PAR-2) inhibitor, for the preparation of a medicament for the treatment of a sensory neuropathy induced by poisoning with a marine sodium channel-activating neurotoxin.

It is thus herein described a method for treating a sensory neuropathy induced by poisoning with a marine sodium channel-activating neurotoxin in a subject in need thereof, said method comprising the administration of a therapeutically effective amount of protease-activated receptor-2 (PAR-2) inhibitor to said subject.

As used herein, the term "poisoning (or intoxication) with a marine sodium channel-activating neurotoxin", abbreviated herein as "neurotoxic marine poisoning", refers to the poisoning or intoxication of a subject by a sodium channel-activating neurotoxin present in marine organisms such as fish or shellfish (e.g. clams, oyster, mussels, etc.). By "neurotoxin", it is meant herein an active agent capable of interfering with the normal function of the nervous system of a subject exposed to said agent. In the context of the present invention, the neurotoxin is a sodium channel-activating toxin, i.e. it is a neurotoxin capable of interfering with the sodium channel function of the nervous system of a subject exposed thereto, by triggering the passing of sodium through said channel. Poisoning with such neurotoxin can be typically caused by ingestion of fish or shellfish contaminated with neurotoxin-producing microorganisms, or following dermal exposure (e.g. during swimming) or inhalation of neurotoxin aerosols (e.g. on the beach, via onshore winds, etc.). Upon exposure, these neurotoxins have the particularity to trigger, even in a nanomolar range, a rapid onset of symptoms, among which gastrointestinal symptoms (e.g. diarrhea, vomiting, nausea, etc.), neurological symptoms (e.g. peripheral and/or central neurological symptoms), cardiovascular symptoms (e.g. bradycardia, hypotension, tachycardia, etc.), and/or respiratory symptoms (e.g. respiratory irritation, respiratory distress, etc.), though these symptoms can vary between individuals. The present invention focuses on the treatment of a particular subset of these clinical features, namely sensory neuropathy.

The term "sensory neuropathy" or "peripheral sensory neuropathy" refers herein to a disease affecting the somatosensory system in a subject. It is generally characterized by an abnormal nerve function in said system, such as a loss of nerve function (e.g. numbness) and/or a gain of nerve function (e.g. itch, pain). Sensory neuropathy is primarily mediated by affected sensory nerves of the peripheral nervous system (also known as peripheral sensory nerves, or somatic primary afferent nerves) of a subject, but can also involve non-neuronal cells, such as glial cells, cells of the immune system and/or keratinocytes. Indeed, glial and immune cells can contribute, both at the peripheral and the spinal levels, to the initiation and/or the maintenance of sensory disturbances. Recent studies have also shown evidence that keratinocytes can modulate sensory transduction, including in neuropathic conditions. The data presented herein demonstrates the role of sensory neurons and keratinocytes, both in mono- and co-culture, in the sensory effects induced by marine sodium channel-activating neurotoxins.

In the context of the present invention, different types of sensory neuropathy can manifest themselves upon neurotoxic marine poisoning, among which pruritus (also known as itch, or a desire to scratch), paresthesia (e.g. numbness, tingling, pins-and-needles sensation, etc.), dysesthesia (e.g. burning pain, electrical sensations, etc.), allodynia (e.g. cold allodynia, i.e. pain triggered by a cold stimulus), myalgia (muscle pain), arthralgia (joint pain), dysuria (painful urination), and dental pain, represent herein particular preferred embodiments. A sensory neuropathy can notably affect different parts of the subject body such as extremities (e.g. arms, fingers, legs, feet) or face (e.g. lips, mouth), and/or even disturb temperature perception (loss of cold and/or hot sensation). For example, paresthesia can affect the perioral area (i.e. perioral paresthesia) and/or extremities of peripheral body parts (i.e. acral paresthesia).

The present invention therefore aims at providing a treatment of any of the above sensory neuropathy induced by neurotoxic marine poisoning, whether said poisoning is recent or not. Indeed, after an initial or acute poisoning with such toxin, peripheral sensory symptoms can sometimes become chronic, lasting weeks to months, sometimes years, or even re-emerge later on when exposed to seafood that does not produce symptoms in other individuals or upon consumption of foods such as alcohol, peanuts or meat products. Thus, in a preferred embodiment, the invention aims at treating an initial or chronic sensory neuropathy induced by poisoning with a marine sodium channel-activating neurotoxin, or a recurrence thereof.

Generally speaking, the term "treatment" or "treating" means obtaining a desired physiological or pharmacological effect depending on the degree of severity of the symptom or disorder of interest, or risks thereof, i.e. herein, depending on the degree of severity of a symptom or disorder induced by neurotoxic marine poisoning, or risks of developing such symptom or disorder. The effect may be prophylactic in terms of a partial or complete prevention of the symptom or disorder and/or may be therapeutic in terms of a partial or complete cure of the symptom or disorder. The term "prophylactic" characterizes the capacity to avoid, or minimize the onset or development of a symptom or disorder before its onset (for example, after exposure to a marine sodium channel-activating neurotoxin, but before the onset of associated symptom). The term "therapeutic" refers to the capacity to inhibit the symptom or disorder (i.e. arresting the development thereof), and/or to relieve said symptom or disorder (i.e. regression leading to an improvement). In the context of the invention, a prophylactic effect is generally said to be achieved when e.g. an asymptomatic subject poisoned with a marine sodium channel-activating neurotoxin remains asymptomatic or quasi-asymptomatic after treatment according the invention (for example, no development of a sensory neuropathy despite poisoning), while a therapeutic effect is typically said to be achieved when e.g. a symptomatic subject poisoned by a marine sodium channel-activating neurotoxin recovers after treatment according to the invention (for example, partial or complete relief of a sensory neuropathy).

As indicated above, the treatment according to the invention can be achieved by administering a therapeutically effective amount of a PAR-2 inhibitor to a subject in need thereof, using any suitable scheme of administration. For instance, said administration can be performed orally, topically, transdermally or parenterally such as by subcutaneous injection, intravenous injection, intramuscular injection or intraperitoneal injection, or any combinations thereof, depending on the type of sensory neuropathy affecting the subject. The dose and/or scheme of administration can be easily determined and adapted by the skilled practitioner, in accordance with the age, weight and/or severity of sensory neuropathy from which the subject suffers.

It would further be readily understood that the "subject" to be treated according to the invention possesses at least a peripheral nervous system and a central nervous system, which interact with each other. Accordingly, preferred subjects according to the invention include vertebrates, preferably mammals, still preferably humans.

In a preferred embodiment, the sensory neuropathy induced by neurotoxic marine poisoning is mediated, inter alia, via the activation of voltage-gated sodium channels (VGSCs) by the neurotoxin. In other words, the marine neurotoxin according to the invention binds to voltage-gated sodium channels, thereby triggering their activation, i.e. is a "voltage-gated sodium channel-activating neurotoxin". Indeed, such specific mechanism of action contributes, at least in part, to the peripheral sensory symptoms observed in neurotoxic marine poisoning.

"Voltage-gated sodium channels (VGSCs)" or "Nav channels (Nav)" are well-known in the art as large integral membrane proteins forming ion channels, which conduct sodium ions (Na+) through a cell membrane. In excitable cells such as neurons and myocytes, and certain types of glia, voltage-gated sodium channels are responsible for the rising phase of action potentials. These channels can go through three different states called resting, active and inactive states, which will affect the flow of cellular sodium, and are thus involved in a myriad of cellular processes, among which the increase in intracellular calcium observed by the Inventors upon exposure to a marine sodium channel-activating neurotoxin. These channels typically consist of a main alpha subunit (of about 220-260 kDa) associated with at least one smaller beta subunit (of about 22 to 36 kDa). Their alpha subunit is generally made up of four homologous domains, namely I-IV, each of which possessing six transmembrane helices, namely S1-S6, with cytoplasmic N- and C-termini. Each of these four major domains can be divided into a voltage sensing domain (S1-S4) and a pore-forming P domain (S5-S6). In addition to regulating channel expression and gating, their beta subunit is a member of the immunoglobulin (Ig) superfamily cell adhesion molecules (CAMs) and regulates cell adhesion and migration. In a preferred embodiment, the voltage-gated sodium channels activated by the marine neurotoxin according to the invention are tetrodotoxin-sensitive (TTX-s) and/or tetrodotoxin-resistant (TTX-r), such as any of the Nav1.1 to Nav1.9 channels isoforms that have been identified to this day in mammalian cells.

In the context of the present invention, the marine neurotoxin more precisely activates voltage-gated sodium channels by binding to the alpha subunit of said channels, more particularly by binding to the neurotoxin binding site 5 of said subunit. Said site is more particularly located in the transmembrane helices S6 (in domain I) and S5 (in domain IV) of the alpha subunit of VGSCs channels, as reported by Stevens et al (2011). Interaction of these types of marine neurotoxins with this unique binding site is known to cause a shift in the voltage dependence of VGSCs activation, resulting in an increase in sodium membrane permeability at the resting membrane potential and a subsequent membrane hyperexcitability.

Examples of marine neurotoxins capable of binding to the alpha subunit of voltage-gated sodium channels (VGSCs), more particularly of binding to the neurotoxin binding site 5 receptor of said subunit, include, without limitation, ciguatoxins, brevetoxins, active metabolites thereof, and any combinations thereof. "Ciguatoxins" and "brevetoxins" are cyclic lipid-soluble polyether neurotoxins typically produced by marine dinoflagellates and/or raphydophytes, and which are capable of contaminating fish or shellfish notably through food chain transfer. These neurotoxins are tasteless, odorless, and heat- and acid-stable. Ciguatoxins are mainly responsible for seafood poisoning known as "Ciguatera" or "Ciguatera Fish Poisoning (CFP)" commonly observed in tropical and subtropical regions, while brevetoxins are associated to "Neurologic Shellfish Poisoning (NSP)" which has been reported inter alia in the Gulf of Mexico coasts (Texas and Florida, USA) and New Zealand. Interestingly, CFP and NSP overlap mainly with regard to their peripheral sensory neurological symptoms. Nevertheless, the degree of severity of these sensory symptoms can vary depending on the nature and/or amount of toxins to which the subject has been exposed, due notably to the existence of a large variety of toxin congeners and their difference in potency. Besides, neurotoxins are generally produced by microorganisms as part of a mixture of active agents. Accordingly, the skilled practitioner would readily understand that the term "a neurotoxin" can designate herein one neurotoxin (a specific structure) or a combination of neurotoxins which are structurally distinct but functionally equivalent (i.e. congeners). Thus, following clinical evaluation of a subject presenting a sensory neuropathy for which a marine neurotoxin is suspected, it might be advisable to identify and quantify the main causative neurotoxin, so as to adapt accordingly the dose and/or scheme of the treatment proposed by the present invention. To do so, a suitable extract of meal remnants or a bodily fluid sample (e.g. blood) of the diseased subject can be analysed, for example via an in vitro assay characterizing the Nav-dependent cytotoxicity of the toxin (Dechraoui et al. 1999, Dickey et al. 1999, Dechraoui et al. 2007), an in vitro assay characterizing the toxin binding affinity for Nav (Dechraoui et al. 1999), and/or a liquid chromatography-mass spectrometry-based method that can characterize the toxin structure and its quantity (Abraham et al. 2008, Lewis et al. 2009). The in vitro mouse neuroblastoma cell assay can also be directed to detect either toxins activating voltage-gated sodium channels (VGSCs) (such as ciguatoxins and brevetoxins), or the ones blocking said channels (Manger et al. 1995).

To this day, over 40 molecular structures (i.e. congeners) of ciguatoxins and brevetoxins have been reported in the literature, which can be classified in subgroups according to their origins and/or carbon backbone among: Pacific Ciguatoxins (P-Ciguatoxins, also referred as P-CTX), Caribbean Ciguatoxins (C-Ciguatoxins, also referred as C-CTX), Indian ciguatoxins (I-Ciguatoxins, also referred as I-CTX), type A brevetoxins (type A PbTx, also referred as BTX-A group), and type B brevetoxins (type B PbTx, also referred as BTX-B group), as reported below.

Accordingly, in a preferred embodiment, the marine sodium channel-activating according to the invention can comprise or consist of a ciguatoxin and/or a brevetoxin selected from:

P-Ciguatoxins (P-CTX) having the formula (I)

(I)

[Chemical structure of P-Ciguatoxin with rings A-M labeled, showing R1 and R4 substituents]

wherein R1 is a $C_2$-$C_6$ alkene group optionally substituted by at least one hydroxyl group (—OH) or by the group —O-AN, AN being an anthroylester, and R4 is H or OH,
preferably wherein R1 is selected from the group consisting of:
CH=CH—CHOH—CH$_2$OH,
CH=CH—CH=CH$_2$, and
CH=CH—CHOH—CH$_2$O-AN, and
R4 is H or OH,
preferably wherein
R1 is CH=CH—CHOH—CH$_2$OH and R4 is OH (CTX-1b),
R1 is CH=CH—CHOH—CH$_2$OH and R4 is H (CTX-2A2),
R1 is CH=CH—CHOH—CH$_2$O-AN and R4 is OH (anthroylester-CTX-1b),
R1 is CH=CH—CH=CH$_2$ and R4 is H (CTX-4b), or
R1 is CH=CH—CHOH—CH$_2$OH and R4 is H (CTX-4a);
or derivatives thereof such as 52-epi CTX-1b, 54-epi CTX-1b, 52-epi 54-epi CTX-1b1b, 7-oxo CTX-1b, 7-hydroxy CTX-1b, 4-hydroxy-7-oxo CTX-1b, 54 deoxy-50-hydroxy CTX-1b, 52-epi-54-deoxy CTX-1b (also known as CTX-2), 54-deoxy CTX1b (also known as CTX-3), M-seco CTX-4b, 52-epi CTX-4b (also known as CTX-4a), M-seco CTX-4a;
C-Ciguatoxins (C-CTX) having the formula (II)

wherein R2 is H or OH, R3 is H or OH, and R4 is H,
preferably wherein R2 and R3 (sp$^3$C) are OH, and R4 is H (C-CTX-1, also known as CTX2A1), or R2 to R4 are H (CTX-3c);

or derivatives thereof such as 56-epi-C-CTX-1 (also known as C-CTX-2), 49-epi CTX-3c (also known as CTX-3b), M-seco CTX-3c, M-seco CTX-3c methyl acetal, 51-hydroxy CTX-3c, 51-hydroxy-3-oxo CTX-3c, A-seco-51-hydroxy CTX-3c, 2,3-hydroxy CTX-3c, 2,3-dihydro-2-hydroxy CTX-3c, 2,3-hydro-51-hydroxy-2-oxo CTX-3c, 2,3-dihydro-2,3-dihydroxy CTX-3c, 2,3-dihydro-2,3,51-trihydroxy CTX-3c, 2,3,51-trihydroxy CTX-3c, 2-hydroxy CTX-3c, A-seco-2,3-dihydro-51-hydroxy CTX-3c;

Indian ciguatoxins (I-CTX), preferably selected from the group consisting of I-CTX-1, I-CTX-2, I-CTX-3, I-CTX-4, I-CTX-5 or I-CTX-6 (Hamilton et al. 2002a and 2002b, Diogene et al. 2017);

(II)

[Chemical structure of C-Ciguatoxin with rings A-M labeled, showing R2, R3, and R4 substituents]

Type A brevetoxins (type A PbTx) having the formula (III)

(III)

[Chemical structure of Type A brevetoxin]

wherein R is a $C_2$-$C_6$ alkene group optionally substituted by at least one hydroxyl group (—OH) or aldehyde group (—CHO), R being preferably selected from the group consisting of:
  $CH_2C(=CH_2)CHO$ (PbTx-2), optionally substituted with an acetylated hydroxyl group in position 38 (PbTx-5) or comprising an epoxide group in position 27-28 (PbTx-6),
  $CH_2C(=CH_2)CH_2OH$ (PbTx-3), and
  $CH_2CH(CH_3)CH_2OH$ (PbTx-9);

Type B brevetoxins (type B PbTx) having the formula (IV)

(IV)

[Chemical structure of Type B brevetoxin]

wherein R is a $C_2$-$C_6$ alkene group optionally substituted by at least one hydroxyl group (—OH) or aldehyde group (—CHO), R being preferably selected from the group consisting of:
  $CH_2C(=CH_2)CHO$ (PbTx-1),
  $CH_2C(=CH_2)CH_2OH$ (PbTx-7), and
  $CH_2CH(CH_3)CH_2OH$ (PbTx-10);
or
  any combinations thereof.

Ciguatoxin and brevetoxin active metabolites have also been reported in the literature, and are accordingly encompassed by the present invention (Lawrence et al. 2011, Ikehara, et al. 2017). The term "metabolites" refers to chemical entities that are modified by the host metabolism, the host preferably being in the present context either the fish or shellfish contaminated by a ciguatoxin and/or a brevetoxin, or that are modified by the subject to be treated according to the invention. "Active metabolites" thus refers to metabolites that retain all or part of the native activity of the chemical entity that has been metabolized; herein, this means that ciguatoxin and brevetoxin active metabolites retain at least the capacity to activate PAR-2, more preferably via Cathepsin S as further reported below.

In a preferred embodiment, the marine sodium channel-activating neurotoxin according to the invention comprises or consists of a ciguatoxin, preferably a P-CTX, more preferably CTX-2 (also known as 52-epi-54-deoxy CTX-1b).

Yet, in another preferred embodiment, the marine sodium channel-activating neurotoxin according to the invention comprises or consists of a brevetoxin, preferably a PbTx type B, more preferably PbTx-1.

According to the different aspects and embodiments of the invention, the term "PARs" or "Protease-Activated Receptors" refers to a family of G-protein coupled receptors (GPCRs) comprising PAR-1, 2, 3, and 4. PARs are typically activated by enzymes which proteolytically cleave a portion of their N-terminal region. This cleavage exposes a region of the N-terminal extracellular domain (called the "tethered ligand") which is believed to bind to residues contained within the second extracellular loop of the PAR receptors, resulting in the stabilization of an active conformation. "PAR-2" is expressed in numerous cells (e.g. epithelial, immune and endothelial cells) and in nerve fibers, notably in skin, and is activated by several host and pathogen-derived serine proteases, including trypsin, tryptase, matriptase, kallikreins (KLK 2/4/5/6/14), Factor Xa, Factor VIIa, granzyme A, cathepsin G, cathepsin S, elastase, acrosin, HAT, TMPRSS2, chitinase, bacterial gingipains, Der P1-3, Pen C13 and testisin—but not thrombin contrary to PAR-1, 3, and 4. PAR-2 activation by these proteases can trigger multiple signaling pathways, including intracellular calcium ([Ca$^{2+}$]i), MAPK, ERK (ERK1/2), cAMP, Rho kinase and/or nuclear factor kappa B pathways, and is therefore involved in a myriad of physiological and pathological processes. A "PAR-2 inhibitor" according to the invention thus refers to an active agent capable of inhibiting PAR-2 activation, in particular at least one PAR-2 signaling pathway. PAR-2 can be activated via two distinct signaling pathways: the canonical PAR-2 pathway and the biased PAR-2 pathway. Upon PAR-2 activation via the "canonical pathway" (for example, via trypsin), a cascade of specific cellular events is triggered: without being bound by theory, activated PAR-2 generally couples to the Gaq/11 protein to activate phospholipase C (PLC), leading to the hydrolysis of phosphatidylinositol bisphosphate (PIP2), Ca$^{2+}$ mobilization into the cytosol from the endoplasmic reticulum, and activation of protein kinases C and D, leading to TRPV4, TRPV1 and/or TRPA1 sensitization. The activation of PAR-2 also signals through (3-arrestin associated with subsequent internalization of PAR-2, and ERK1/2. The signalosome complex prevents ERK translocation in the nucleus and allows cytosolic phosphorylation of substrates. Internalized PAR-2 then moves into lysosomes where it may be degraded or recycled. By contrast, when PAR-2 is activated via the "biased pathway", PAR-2 is typically cleaved at a distinct site from the canonical site, thereby triggering a different cascade of cellular events that do not generally signal through β-arrestin pathway and do not generally internalize PAR-2. In the "biased pathway", PAR-2 appears to couple to the Gas protein to activate protein kinase A. Nevertheless, like in the canonical PAR-2 pathway, this also leads to sensitization of TRP channels such as TRPV4, TRPV1 and/or TRPA1 through phosphorylation, which in turn facilitate intracellular entry of calcium. An increase in intracellular calcium is thus a common feature to both the canonical and the biased PAR-2 pathways. In the context of the present invention, the PAR-2 inhibitor preferably inhibits at least the intracellular calcium pathway (i.e. it inhibits an increase in intracellular calcium following PAR-2 activation). In a preferred embodiment, the PAR-2 inhibitor is PAR-2 specific (i.e. it does not inhibit other PARs, or at least minimally), and/or acts as a PAR-2 antagonist. The term "PAR-2 antagonist" refers herein to a PAR-2 inhibitor capable of binding directly to PAR-2, and can be a PAR-2 biased antagonist or a PAR-2 full antagonist. By "PAR-2 biased antagonist", it is meant a PAR-2 antagonist which inhibits at least one, but not all, of the PAR-2 signaling pathways as described herein, while the term "PAR-2 full antagonist" designates a PAR-2 antagonist which inhibits all PAR-2 signaling pathways, i.e. both the canonical and biased PAR-2 pathways. A particularly preferred PAR-2 inhibitor according to the invention is a PAR-2 full antagonist, or in other words is a PAR-2 inhibitor that inhibits the canonical and biased PAR-2 pathways. Inhibition of PAR-2 activation can be assessed by methods well-known in the art, including, inter alia, PAR-2 intracellular Ca2+ assay (see for example Suen et al. 2014, or section 1.3, of the Examples below).

In a preferred embodiment, the protease-activated receptor-2 (PAR-2) inhibitor according to the invention is a small molecule, a peptide, a polypeptide, a polynucleotide or any combinations thereof.

The term "small molecule" refers to a low molecular weight organic molecule, i.e. an organic molecule having generally a molecular weight below 900 Daltons.

The terms "peptide" and "polypeptide" according to the invention designate a sequence of amino acids joined by peptide bonds (—NHCO—). Generally, peptides consist of between 2 and 50 amino acids, whereas polypeptides comprise more than 50 amino acids. Particularly preferred peptides and polypeptides according to the invention are pepducins and antibodies, respectively. "Pepducins" (also generally referred as "lipidated peptides") are cell-penetrating peptides that act as intracellular modulators of signal transference from GPCRs and typically consist of a short peptide derived from a GCPR tethered to a hydrophobic moiety e.g. to a lipid (Carlson et al. 2012). "Antibodies" are polypeptides capable of specifically recognizing an antigen (herein, PAR-2 or an antigen activating PAR-2). To do so, the antibody's paratope interacts with the antigen's epitope. An antibody typically consists of four polypeptides—two full-length light chains and two full-length heavy chains—which are joined to one another with disulfide bonds to form a Y-shaped protein. Herein, the term antibody encompasses as well antibody fragments (Fab, Fv, ScFv, HCAb, sdAb, etc.) and antibody mimetics (ABDs, adhirons, affibodies, affimers, armadillo repeat proteins, DARPins, pronectins, transbodies, trimers X, etc.) (Immunobiology by Janeway et al., 5th edition, Garland publishing, 2001; Therapeutic Monoclonal Antibodies: From Bench to Clinic by An et al., Wiley editions, 2009; Skrlec et al. 2015).

As used herein, the term "polynucleotide" refers to a precise succession of natural nucleotides (e.g., A, T, G, C and U), or synthetic nucleotides, corresponding to a single-stranded or double-stranded DNA such as cDNA, genomic DNA, ribosomal DNA, and the transcription product of said DNA, such as RNA. This term encompasses nucleic acids encoding a peptide or polypeptide of interest, as well as nucleic acids, which can hybridize to a nucleic acid of reference. Particularly preferred polynucleotides according to the invention are RNAi or aptamers. "RNAi" refers to a polynucleotide that can inhibit expression of a target gene by RNA interference mechanism; it includes, without limitation, shRNA, siRNA, miRNA (Sohail et al. 2004, Gene Silencing by RNA Interference: Technology and Application 1$^{st}$ Edition, ISBN 9780849321412). The term "aptamer" refers to a DNA or RNA molecule that is target specific and has a high affinity for said target, and which can be prepared by a well-known in vitro selection process called <<SELEX>> (Systemic Evolution of Ligands by Exponential enrichment, as notably described in WO 91/19813).

In a preferred embodiment, the protease-activated receptor-2 (PAR-2) inhibitor according to the invention interacts directly with PAR-2. In other words, the PAR-2 inhibitor according to the invention is preferably a PAR-2 antagonist, such as a PAR-2 biased antagonist or a PAR-2 full antagonist. More preferably, the PAR-2 inhibitor is a PAR-2 full antagonist. Such PAR-2 inhibitors have been extensively reported in the scientific and patent literature, and are thus well-known to the skilled practitioner (Yau et al. 2016a, incorporated herein by reference). Below is provided non-exhaustive list of these inhibitors which can be suitable according to the invention.

Examples of small molecules suitable for inhibiting PAR-2 activation include, without limitation, 5-isoxazolyl-Cha derivatives such as GB83 and GB88 as well as related derivatives thereof e.g. Carvedilol, Loratadine, Nefazodone, Astemizole (WO2013013273, US2050038402, Barry et al 2010, Xu et al 2015, Yau et al 2016b, Lieu et al 2016), piperazine and piperidine derivatives (KR2010038919, WO2012101453), quinazoline derivatives (KR2011130259, Cho et al 2015), benzidazole derivatives (WO2012026765, WO2012026766), amidine derivatives (WO2014020350, WO2014020351), benzothiazine-carboxamide derivatives (KR2015044675), imidazopyridazine derivatives (WO2015048245), bicatulamide, 1,7-Bis(4-methoxyphenyl)-3,5-heptanedione and derivates thereof (WO2012143576), and any combinations thereof (all the above-mentioned patent and scientific publications being incorporated herein by reference).

The term "derivative" means herein a molecule sharing a basic structure of reference (such as an amidine structure, etc.), and/or a putative binding site to a target of interest. For example, the derivative can be identified via computational modeling by screening a drug database (e.g. via virtual docking of a known PAR-2 antagonist in a PAR-2 homology model compared with the docking of a putative PAR-2 ligand in the same homology model).

Examples of pepducins suitable for inhibiting PAR-2 activation include, without limitation, P2pal-18S (N-pal-RSSAMDENSEKKRKSAIK-NH2, i.e. SEQ ID NO: 1), P2pal-14GQ (N-pal-GDENSEKKRKQAIK)-NH2, i.e. SEQ ID NO: 2), P2pal-21 (N-pal-RMLRSSA-MDENSEKKRKRAIK-NH2, i.e. SEQ ID NO: 3) (Sevigny et al. 2011, incorporated herein by reference) and those described in WO2012139137 (incorporated herein by reference). N-pal represents herein an N-palmitoyl group, while NH2 refers to an amino group.

Examples of non-lipidated peptides suitable for inhibiting PAR-2 activation, preferably directly, include, without limitation, FSLLRY-NH2 (SEQ ID NO: 4) and LSIGRL-NH2 (SEQ ID NO: 5) (Al-Ani et al. 2002, Zhu et al. 2017), SLAGKV (SEQ ID NO: 6) (Chen et al. 2011), 2-aminothiazo-4-yl-LIGRL-NH2 (SEQ ID NO: 7) also referred as C391 (Boitano et al. 2015), as well as peptides described in WO2012090207 such as SHDFRDHA (SEQ ID NO: 8), in WO2013064583 such as Ac-FFWFHV-NH2 (SEQ ID NO: 9), and/or in KR2011118210 such as RRFSLLRY-NH2 (SEQ ID NO: 10) (all the above-mentioned patent and scientific publications being incorporated herein by reference). A preferred non-lipidated peptide PAR-2 inhibitor according to the invention is 2-aminothiazol-4-yl-LIGRL-NH2 (SEQ ID NO: 7), as it is capable to inhibit not only PAR-2 calcium signaling, but also ERK1/2 phosphorylation (Boitano et al. 2015).

Examples of antibodies suitable for inhibiting PAR-2 activation, preferably directly, include, without limitation, antibodies described in WO2011031695 such as antibody H4H581P, in WO2007092640 such as antibody 47.7, in WO2009005726 such as antibody 1A1, and in WO2010017086 (all the above-mentioned patent publications being incorporated herein by reference).

Examples of RNAi suitable for inhibiting PAR-2 activation, preferably directly, include, without limitation the siRNA r(UUA AAC AGG UUC CAC AUC C)dTdA (SEQ ID NO: 11) as described by Dommisch et al. 2007, incorporated herein by reference.

In a preferred embodiment, the protease-activated receptor-2 (PAR-2) inhibitor according to the invention is GB83 or a derivative thereof such as GB 88, Carvedilol, Loratadine, Nefazodone, or Astemizole. GB83 (PAR-2 full antagonist) and GB88 (PAR-2 biased antagonist) can indeed inhibit PAR-2 calcium signaling, while the derivatives Carvedilol, Loratadine, Nefazodone, or Astemizole inhibit both PAR-2 calcium mobilization and ERK1/2 phosphorylation (Yau et al. 2016b).

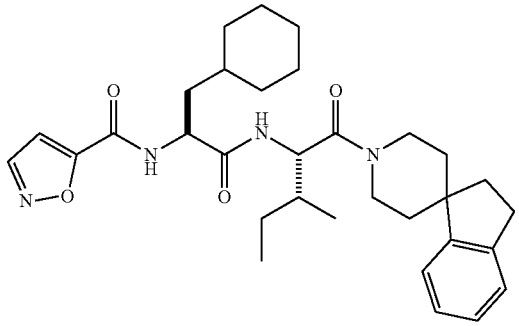

GB83 (V)

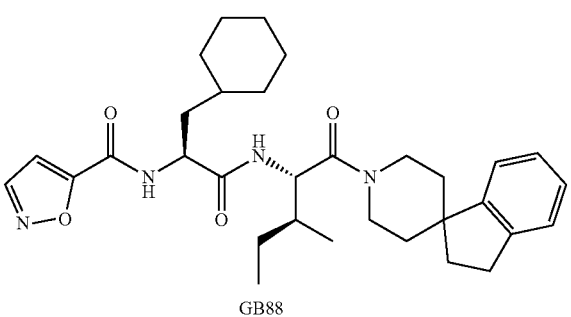

GB88 (VI)

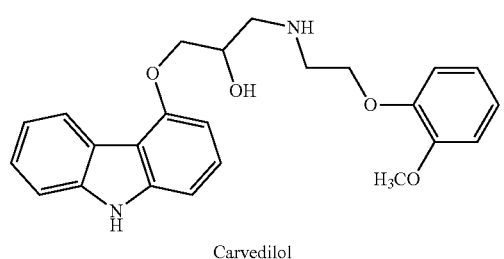

Carvedilol (VII)

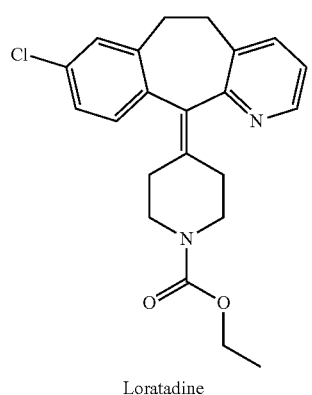

Loratadine (VIII)

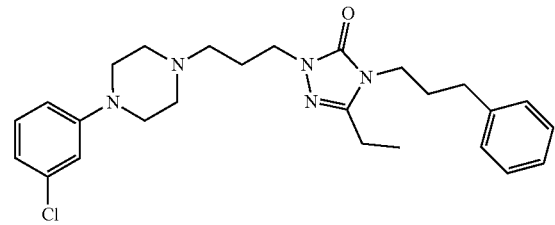

Nefazodone

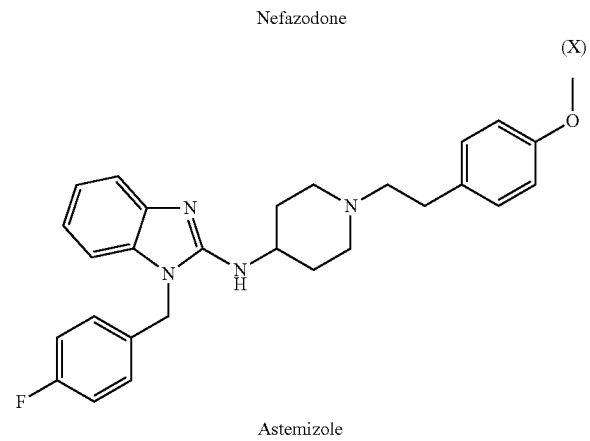

Astemizole

More preferably, the protease-activated receptor-2 (PAR-2) inhibitor according to the invention is GB83 or GB88, even more preferably is GB83.

The protease-activated receptor-2 (PAR-2) inhibitor according to the invention may also target PAR-2 in an indirect manner, for example by inhibiting a cellular target upstream of PAR-2 signaling. The Inventors indeed showed that cathepsin-S-mediated PAR-2 signaling is a pathway contributing to the pathophysiology of sensory effects induced by neurotoxic marine poisoning according to the invention. The data presented herein notably demonstrate that key feature(s) of neurotoxic marine poisoning mediated by sodium channel-activating neurotoxins (e.g. sensory neuropeptides release and/or intracellular calcium release) was completely abrogated by specific inhibition of cathepsin S, while this feature was only partially diminished using a broad-spectrum cysteine protease inhibitor.

Accordingly, in a preferred embodiment, the protease-activated receptor-2 (PAR-2) inhibitor according to the invention inhibits cathepsin-S-mediated PAR-2 signaling. More precisely, the protease-activated receptor-2 (PAR-2) inhibitor according to the invention preferably interacts directly with cathepsin S, and can be referred herein as a Cathepsin S inhibitor.

"Cathepsin S" or "Cat-S" designates herein a lysosome cysteine protease of the papain family that is the only one of 11 cysteine protease members (Cat B, C, F, H, L, K, O, S, V, W, X/Z) to maintain a proteolytic activity at neutral pH, notably following its release in the extracellular space. Cysteine proteases are expressed in many cells, especially in antigen-presenting cells, including e.g. microglial cells, B-lymphocytes, and dendritic cells; they accordingly play important roles in human biology and various diseases including atherosclerosis, emphysema, osteoporosis, chronic inflammation and immune disorders. To this day, cathepsin S has more particularly been identified as being key in regulating antigen presentation and immunity, as well as angiogenesis (and hence cancer). Cathepsin S can proteolyze many targets, among which the chemokine fractalkine (sFKN), extracellular matrix proteins, and PAR-2. Cat-S has more particularly been reported to activate PAR-2 by unmasking a specific receptor-activating tethered ligand hexapeptide in PAR-2 N-terminus, namely KVDGTS (SEQ ID NO: 12) (Elmariah et al. 2014), which differs from the one unmasked upon trypsin activation. A "cathepsin S inhibitor" or "cat-S inhibitor" according to the invention thus refers to an active agent capable of inhibiting cathepsin S proteolytic activity, in particular the cathepsin-S-mediated PAR-2 signaling. In a preferred embodiment, the cat-S inhibitor is cat-S specific (i.e. it does not inhibit other cathepsins, or at least minimally), and/or acts as a cat-S antagonist. The term "cat-S antagonist" refers herein to a cat-S inhibitor capable of binding directly to cat-S, and can be a cat-S biased antagonist or a cat-S full antagonist. By "cat-S biased antagonist", it is meant a cat-S antagonist which inhibits proteolysis of at least one, but not all, cat-S targets (herein at least PAR-2), while the term "cat-S full antagonist" designates a cat-S antagonist which inhibits proteolysis of all cat-S targets. Inhibition of cat-S activation can be assessed by methods well-known in the art, including, inter alia, the intracellular Ca2+ assay (Elmariah et al. 2014), but also the Cathepsin-S activity assay as described in section 1.7 of the Examples below.

Cathepsin S inhibitors/antagonists have been more recently reported both in the scientific and patent literature, and are thus well-known to the skilled practitioner (Wiener et al. 2010, Lee-Dutra et al. 2011, both incorporated herein by reference).

Examples of suitable Cat-S inhibitors according to the invention include, without limitation, small molecules, peptides, polypeptides, polynucleotides and the likes such as the dipeptidyl α-keto-β-aldehyde named Cbz-Phe-Leu-COCHO (also referred as Z-FL-COCHO) (Walker et al. 2000), JNJ 10329670 (also known as 1H-Pyrazolo(4,3-C)pyridine, 1-(3-(4-(6-chloro-2,3-dihydro-3-methyl-2-oxo-1H-benzimidazol-1-yl)-1-piperidinyl)propyl)-4,5,6,7-tetrahydro-5-(methylsulfonyl)-3-(4-(trifluoromethyl)phenyl)-) (Thurmond et al. 2004), the vinyl sulfone inhibitor LHVS (Riese et al. 1998), CLIK-060 and CLIK-0172 (Katunuma et al. 1999), R05459072 (also known as Petesicatib) (Tato et al. 2017), and also the Cat-S inhibitors described in Tsai et al. 2014, WO2007128987, WO2009144450, WO2007144379, WO2005082876, WO200069855, WO2010034788, WO2010034789, WO2010034790, WO2009112826, WO2009112839, WO2005107464, WO2005039496, WO2005028454, WO2005063742, WO2005074904, WO2006102243, WO2006102423, WO2009055467 (Virobay), WO2005040142, WO2007137738, US20090275523, WO2003075836, WO2005019161, WO2005021487, WO2005056529, WO2006056047, U.S. Pat. No. 6,576,630, WO2008028301, WO2006128287, WO2005028429, WO2006034006, WO2006034004, WO2006060810, WO2006102535, WO2008042968 (Virobay), WO2006060494, WO2004000825, WO2004054987, WO2004083182, WO2004000819, WO2004000843, WO2007148064, WO2003020721, WO2006018284, WO2003020278, WO2007080191, WO2009010491, WO2008100618, WO2008100621, WO2008100622, WO2008100620, WO2008100635, WO2004084842, WO2004084843, WO2004112709, WO2005018568, WO2005034848, WO2007128987, WO2008044076, WO2006064286 (all the above-mentioned patent and scientific publications being incorporated herein by reference).

In a preferred embodiment, the protease-activated receptor-2 (PAR-2) inhibitor according to the invention is Cbz-Phe-Leu-COCHO or a derivative thereof.

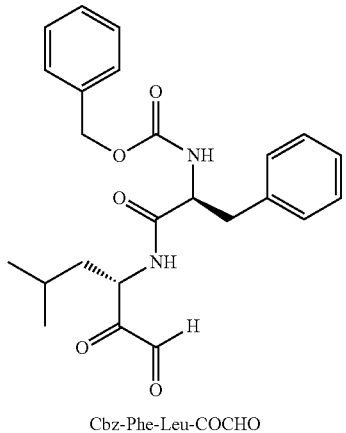

(XI)

Cbz-Phe-Leu-COCHO

In a more preferred embodiment of the present invention, the marine sodium channel-activating neurotoxin comprises or consists of a ciguatoxin, preferably a P-CTX ciguatoxin, more preferably CTX2, and the protease-activated receptor-2 (PAR-2) inhibitor is Cbz-Phe-Leu-COCHO, GB83, or a derivative thereof as described above, preferably is GB83.

Yet, in another preferred embodiment of the present invention, the marine sodium channel-activating neurotoxin comprises or consists of a brevetoxin, preferably a PbTx type B brevetoxin, more preferably PbTx-1, and the protease-activated receptor-2 (PAR-2) inhibitor is Cbz-Phe-Leu-COCHO, GB83, or a derivative thereof as described above, preferably is GB83.

The protease-activated receptor-2 (PAR-2) inhibitor used according to the invention can be advantageously comprised in a pharmaceutical composition. In other words, the PAR-2 inhibitor used according to the invention in a form suitable for administration to the subject to be treated.

The pharmaceutical composition may accordingly further comprise a pharmaceutically acceptable excipient. By "pharmaceutically acceptable excipient", it is meant herein a compound of pharmaceutical grade which improves the delivery, stability or bioavailability of an active agent, and can be metabolized by, and is non-toxic to, a subject to whom it is administered. Preferred excipients according to the invention include any of the excipients commonly used in pharmaceutical products, such as, for example, microcrystalline cellulose, lactose, starch, and soybean powder.

For the purposes of the invention, the composition may be in a form suitable for orally, topical, transdermal or parenteral administration, such as a cream, a liquid suspension, or a solid dosage form.

The present invention further proposes a novel in vitro model for studying sensory disorders, in particular sensory disturbances mediated by marine sodium channel-activating neurotoxins. This model is an optimized version of a previous in vitro neuro-cutaneous co-culture system developed by Le Garrec et al. in 2016 (incorporated herein by reference). The Inventors have indeed surprisingly discovered that culturing sensory neurons cells prior to keratinocytes in such co-culture model could synergistically improve the cellular release of sensory neuropeptides, which are key features of many sensory disorders.

Accordingly, in another aspect, the invention pertains to provide an in vitro method for producing a neuro-cutaneous model capable of releasing sensory neuropeptides, said method comprising:

a) growing a population of sensory neurons in a culture medium suitable for neurites formation;
b) growing a population of keratinocytes with the population of sensory neurons obtained in step a) in a culture medium suitable for keratinocytes adherence; and
c) growing the co-population of keratinocytes and sensory neurons obtained in step b) in a culture medium suitable for keratinocytes differentiation.

The term "sensory neuropeptide" refers herein to a naturally occurring peptide generally released by a sensory neuron upon specific stimulation, and which is involved in sensory messages typically transmitted to the central nervous system upon reaching a certain threshold of stimulation. Examples of sensory neuropeptides according to the invention include, among others, substance P (SP) and calcitonin-gene-related peptide (CGRP). In the context of the present invention, a SP and CGRP enzyme immunoassay (EAI) can be performed to check neuropeptide release by the in vitro neuro-cutaneous model.

By "a population of cells", it is meant herein at least two cells. Thus, by "a population of sensory neurons" or "a population of keratinocytes" according to the invention, it is meant at least two sensory neurons or at least two keratinocytes, respectively, as further defined below.

The term "neuron" or "neuronal cell" refers herein to a cell displaying a neuronal phenotype (neuronal morphology, and electrical activity), which forms the basic unit of the nervous system of a subject (The Neuron: Cell and Molecular Biology, by Levitan I B and Kaczmarek L K, 4th edition, 2015, Oxford University Press). "Sensory neurons" or "afferent neurons" are a particular subtype of neurons, which are capable of sensory transduction, i.e., of converting a sensory stimulus into an action potential, which can be transmitted from the peripheral nervous system along axons towards the central nervous system for integration. Particularly preferred sensory neurons according to the invention are dorsal root ganglia (DRG) neurons. In the context of the present invention, the sensory neurons may be cultured in presence of additional cells present in the dorsal root ganglia, including Schwann cells. The neurons are herein said to have reached a satisfying growth once they have formed neurites. "Neurites" represent projections from the cell body of a neuron, of which peripherin, and/or NF200 (Neurofilament-200) are particularly preferred neurites cellular markers.

The term "keratinocyte" refers herein to a cell forming the majority of the outer layer of the skin (epidermis) and that provides a barrier against external aggression or water loss (Keratinocytes: Structure, Molecular Mechanisms and Role in Immunity. Edition by E. Ranzato, Nova Science Publishers, Inc., New York, USA, 2013). Keratinocytes can be isolated from a skin sample such as a human skin sample, according to methods well known in the art. Preferably, the population of keratinocytes is a population of primary epidermal keratinocytes. The keratinocytes are herein said to have reached an adherence stage once they are attached to the surface on which they are grown, and a differentiation stage once they express sensory receptor(s) such as the neurokinin-1 (NK1) receptor (NK1R).

In a preferred embodiment, the co-culture method according to the invention is performed in the same cell culture container. In other words, the sensory neurons and keratinocytes are not grown in two separated cell culture containers, but are rather grown together in the same cell culture container.

The term "culture medium", "growth medium" or "cell medium" according to the invention encompasses any medium comprising growth-promoting components such as growth factors, essential nutrients (e.g. amino acids, carbohydrates, vitamins, minerals), and/or gases (e.g. $CO_2$, $O_2$), and which can regulate the physio-chemical environment (e.g. pH buffer, osmotic pressure, temperature). The culture medium may vary for each cell type, and is generally contained in a vessel in which the cells are grown. Said vessel may be a solid surface, such as a plastic or a glass surface. Preferred culture media according to the invention, include, without limitation, DMEM (Dulbecco's Modified Eagle medium) and KSFM (keratinocyte-serum free medium). A preferred culture medium of step a), and/or of step c), is DMEM, such as DMEM:DMEM/F12 (preferably in a 1:1 ratio), and/or a preferred culture medium of step b) is KSFM such as complete KSFM. The culture medium may be completed with any further useful agent such as antibiotics and/or a corticoid such as hydrocortisone.

In a preferred embodiment, the culture medium of step a), and optionally the one of step c), comprise(s) at least one neurotrophic agent, such as any one of B27, nerve growth factor (NGF), brain-derived neurotrophic factor (BDNF), insulin, or any combinations thereof. By "neurotrophic agent", it is meant herein an agent facilitating the growth of neurons.

In a preferred embodiment, the culture medium of step b) comprises at least one epidermal growth agent, such as epidermal growth factor (EGF) and/or BPE (bovine pituitary extract). By "epidermal growth agent", it is meant herein an agent facilitating the growth of epidermal cells, such as keratinocytes.

In a preferred embodiment, the culture medium of step a), and the one of step c), can comprise extracellular calcium, so as to facilitate neurites formation and keratinocytes differentiation. In a more preferred embodiment, the extracellular calcium concentration in said medium is a physiological concentration, such as a concentration comprised between 0.5 mM and 2.5 mM, preferably between 0.75 mM and 2 mM, more preferably between 1 mM and 1.8 mM.

In contrast, the culture medium of step b) is preferably devoid of extracellular calcium or comprises extracellular calcium at a concentration below a physiological concentration as defined above. In a more preferred embodiment, the extracellular calcium concentration in said medium is comprised between 0.01 mM and 0.4 mM, preferably between 0.05 mM and 0.2 mM, more preferably between 0.075 mM and 0.15 mM. Most preferably, the extracellular calcium concentration in said medium is 0.09 mM.

In a preferred embodiment, step a) is performed for at least 3 days to 10 days, preferably for 5 days to 7 days, and/or step b) is performed for at least 0.75 day (about 18 hours) to 2 days, preferably for 1 day, and/or step c) is performed for at least 0.4 day (about 10 hours) to 1 day, preferably for 0.5 day (about 12 hours) to 0.65 day (about 16 hours).

In another aspect of the present invention, the in vitro neuro-cutaneous model according to the invention may be used for drug screening purposes. In particular, novel drug assays may be provided, which identify therapeutics efficiently stopping, relieving or preventing the sensory disturbances triggered by marine sodium-channels-activating neurotoxins.

In this aspect, the invention pertains to an in vitro screening method for identifying an active agent or combination of active agents useful in treating a sensory neuropathy induced by poisoning with a marine sodium-channels-activating neurotoxin, comprising:

contacting the in vitro neuro-cutaneous model according to the invention, with a candidate agent or a combination of candidate agents;

wherein the detection of PAR-2 inhibition or Cathepsin S inhibition or sensory neuropeptide release inhibition in said model is indicative that said agent or combination of agents is useful in treating a sensory neuropathy induced by poisoning with a marine sodium-channels-activating neurotoxin.

The detection of PAR-2 inhibition or Cathepsin S inhibition or sensory neuropeptide release inhibition can be performed by methods well-known in the art as described above, or according to the methods illustrated in the Examples of the present application.

The present invention will be better understood in the light of the following detailed description of experiments, including examples. Nevertheless, the skilled artisan will appreciate that this detailed description is not limitative and that various modifications, substitutions, omissions, and changes may be made without departing from the scope of the invention.

EXAMPLES

Abbreviations: BDNF, brain-derived neurotrophic factor; BSA, bovine serum albumin; [Ca2+]i, intracellular calcium concentration; Cat-S, cathepsin S; CFP, ciguatera fish poisoning; CGRP, calcitonin gene-related peptide; CTXs, ciguatoxins; DAPI, 4'6-diamindino-2-phenylindole; DMEM, Dulbecco's Modified Eagle Medium; DRG, Dorsal root ganglion; DTT, dithiothreitol; EDTA, ethylenediamine tetraacetic acid; F12, Ham's Nutrient Mixture F-12; KSFM, Keratinocyte-Serum Free Medium; MeOH, methanol; Mrgpr, mas-related G-protein-coupled receptor; Nav, voltage-gated sodium channel; NGF, nerve growth factor; NK1R, neurokinin-1 receptor; PBS, phosphate-buffered saline; PbTx-1, brevetoxin-1; P-CTX-1 and -2, Pacific ciguatoxin-1 and -2; PLL, poly-L-lysin; SEM, standard error of the mean; SP, substance P; TTX, tetrodotoxin.

Material and Methods

Reagents

Dulbecco's Modified Eagle Medium (DMEM), DMEM/Ham's Nutrient Mixture F-12 (DMEM/F12) and trypsin-EDTA (ethylenediamine tetraacetic acid) were purchased from Lonza (Verviers, Belgium). Complete Keratinocyte-Serum Free Medium (KSFM) was prepared with KSFM containing L-glutamine, epidermal growth factor, and bovine pituitary extract obtained as a kit from Life Technologies (Saint Aubin, France) and supplemented with 100 μg/mL Normocin® (Cayla-InvivoGen, Toulouse, France). B27 and dispase were obtained from Life Technologies (Saint Aubin, France). Collagenase IV, poly-L-lysin (PLL), nerve growth factor (NGF), insulin, hydrocortisone, bovine serum albumin (BSA), trypsin from bovine pancreas (as a PAR-2 agonist), E64 (a broad-spectrum cysteine protease inhibitor), dithiothreitol (DTT) and EDTA were provided by Sigma-Aldrich (St. Quentin Fallavier, France). Brain derived neurotrophic factor (BDNF) was purchased from Santa Cruz Biotechnology (Dallas, CA, USA). The protease inhibitor Cocktail was provided from Roche (Meylan, France). Pacific ciguatoxin-2 (P-CTX-2, i.e. 52-epi-54-deoxyCTX1-b, >90% purity) was isolated from moray eel (*Gymnothorax javanicus*) livers as previously described (Lewis et al. 1991). Tetrodotoxin (TTX) (antagonist of Nav channels) and brevetoxin-1 (PbTx-1) were purchased from Latoxan (Valence, France). Stock solution of 1.15 mM of PbTx-1 solubilized in pure methanol (MeOH) and dried and resolubilized in medium while 10 µM of P-CTX-2 was solubilized in MeOH:water (1:1). GB83 (PAR-2 antagonist) was obtained from Axon Medchem (Groninger, Netherland). Z-FL-COCHO (Cat-S inhibitor) was purchased from Merck Millipore (Guyancourt, France). Bisindolylmaleimide X hydrochloride also known as BimX (PKC antagonist, herein at 10 µM), H89 (PKC antagonist, herein at 3 µM), and HC-067047 (TRPV4 antagonist, herein at 10 µM) were purchased to Sigma-Aldrich (Saint Quentin Fallavier, France). Xestospongin C (Inositoltriphosphate receptor (IP3r) antagonist, herein at 5 µM) was purchased to Abcam (Cambridge, UK) and the human recombinant cathepsin S was obtained to R&D systems (Minneapolis, USA). The fluorogenic substrates Ac-Lys-Gln-Lys-Leu-Arg-AMC trifluoroacetate salt and Z-Phe-Arg-AMC were purchased from Bachem (Bubendorf, Switzerland).

Monocultures and Co-Cultures of Primary Rat DRG Neurons and Human Keratinocytes

The rat sensory neurons were obtained as previously described (Le Garrec et al. 2016). Briefly, dorsal root ganglia were extracted from newborn Wistar rats, chemically digested by collagenase IV (200 units/mL) and mechanically dissociated with a fire-polished Pasteur pipette. The neuronal cell suspension was filtered through a 100 mm-nylon cell strainer, centrifuged at 150 g for 5 min and used for the cytosolic $Ca^{2+}$ imaging experiments or co-culture. The animal experimental procedures were performed in accordance with the French Ministry of Agriculture and the European Communities Council Directive 2010/63/UE and approved by the local veterinary authority.

Human skin samples were obtained from healthy adult donors undergoing abdominal reduction surgery after obtaining informed consent. The dissociated human epidermal keratinocytes were obtained as previously described (Le Gall-Ianotto et al. 2012). Briefly, the epidermal layer was separated after digestion with dispase, and the cells were dissociated using a 0.05% trypsin-EDTA solution. The epidermal suspension was filtered through a 100 mm-nylon cell strainer and centrifuged at 400 g for 5 min. The cells were cultured in complete KSFM and detached using trypsin-EDTA for sub-culture. For the cytosolic $Ca^{2+}$ imaging experiments or co-culture, keratinocytes from 2-3 and 8-9 passages were seeded and maintained in complete KSFM for 24 hours before differentiation for 12-16 hours in DMEM:DMEM/F12 1:1.

A previously reported co-culture model (Le Garrec et al. 2016) was subjected to some modifications to obtain better neurite outgrowth, limited neuron clumps and potentiated neuropeptide release. DRG neurons were seeded on 96 well-plates at a rate of one newborn rat per 12-14 wells in DMEM:DMEM/F12 1:1 supplemented with Normocin® (100 µg/mL), B27 (20 µL/mL), NGF (100 ng/mL), insulin (4 µg/mL), BDNF (20 ng/mL) and hydrocortison (10 ng/mL); then, the neurons were incubated at 37° C. in a 5% $CO_2$ humidified atmosphere. After 3 to 7, preferably 3 to 5 days of culture, the medium was gently removed from the wells, and keratinocytes were seeded at a density of 20,000-25,000 cells, preferably 20,0000 cells, per well in complete KSFM. The co-cultures were maintained for 24 h at 37° C. in a 5% $CO_2$ humidified atmosphere to allow for keratinocyte attachment; then, the medium was replaced with DMEM:DMEM/F12 1:1 to induce keratinocyte differentiation for 12-16 hours.

Single Cell Cytosolic $Ca^{2+}$ Video Imaging

For $Ca^{2+}$ imaging, experiments, neuronal cell or keratinocyte suspension was plated on poly-L-lysine (PLL)-coated glass coverslips. Changes in cytosolic $Ca^{2+}$ concentration were measured using Fura-2 probe (Thermo Fisher Scientific, Molecular probes). To do so, cells were loaded with 4 µM Fura-2/AM (Molecular Probes, Invitrogen, Cergy Pontoise, France) plus 2 µM pluronic acid (Gibco) for 30-60 minutes, preferably 30 minutes for neurons and preferably 45 to 60 minutes for keratinocytes, in the dark at 37° C. in a recording medium containing (in mM): 135 NaCl, 5 KCl, 1 $MgCl_2$, 1.8 $CaCl_2$, 10 HEPES, 10 glucose, pH adjusted at 7.45 with NaOH. Cells were washed twice and equilibrated for 10-15 minutes in the same buffer to allow de-esterification of the dye. Ratiometric images of $Ca^{2+}$ signals (fluorescence ratios of the 340/380 nm excitation and 505 nm emission) were obtained using a microscope (IX71, Olympus) equipped with a monochromator illumination system (Polychrome V, TILL Photonics). Emission was collected through a 415DCLP dichroic mirror, by a 14-bit CCD camera (EXiBlue, Qimaging). Image acquisition and analysis were performed with the Metafluor 6.3 software (Universal Imaging, West Chester, PA, USA), at room temperature. Region of interests (ROIs) chosen were soma of clearly defined single DRG neurons or keratinocytes and a dim region was selected as background. At least 50 to 150 regions of interest were defined for each condition. In DRG cultures, DRG neurons were selected according to their morphology and neuronal identity was checked at the end of the experiments by applying KCl. Experiments were performed at room temperature in the HEPES-buffered solution. P-CTX-2 (10 nM) or PbTx-1 (1 M) or their respective control was applied manually to limit amount consumed. Background fluorescence was subtracted from the corresponding images and results were expressed as $\Delta F/F0$.

Culture Treatments

The monocultured or co-cultured cells were treated for 90 min at 37° C. in a 5% $CO_2$ humidified atmosphere with 10 nM P-CTX-2 or 2 µM PbTx-1 as final concentrations or their vehicle control (MeOH 0.05% or DMEM:DMEM/F12 1:1, respectively) in a final volume of 100 µL DMEM:DMEM/F12 1:1 supplemented with Normocin®. In some experiments, pharmacological antagonists were applied (at the concentrations specified below) 15 minutes before the exposure to P-CTX-2 or to PbTx-1. The supernatants from each condition were collected in the presence (for the subsequent SP measurements) or absence (for the subsequent determination of the Cat-S activity) of a protease inhibitor cocktail, centrifuged to remove the floating cells, and stored at −20° C. for the subsequent SP or Cat-S activity measurements.

Substance P (SP) Enzyme Immunoassay (EIA)

The levels of substance P (SP) in the supernatants were quantified using an SP EIA kit (Cayman chemical, Bertin Pharma, Montigny le Bretonneux, France) following the manufacturer's instructions as previously described (Chéret et al. 2014). The levels of the neuropeptide were obtained in pg/mL.

Immunocytochemical Characterization of PAR-2 Internalization

Immunocytochemistry and Confocal Laser-Scanning Microscopy to Characterize PAR-2 Internalization in Human Primary Keratinocytes To examine the internalization of PAR-2, human epidermal keratinocytes cultured as described above on poly-L- lysine (PLL)-coated glass coverslips were incubated in DMEM:DMEM/F12 1:1 containing 10 nM P-CTX-2, 1 µM PbTx-1, 500 nM trypsin from bovine pancreas (as a PAR-2 agonist) or their vehicle controls for 45 min at 37° C. After the treatment, the cells were washed with phosphate-buffered saline (PBS), fixed with 4% cold paraformaldehyde, permeabilized with Triton 0.5% and blocked with 5% bovine serum albumin (BSA). PAR-2 immunolabeling was performed using a rabbit monoclonal IgG anti-PAR-2 antibody (Abcam ab180953, 1:100), followed by the secondary antibody polyclonal IgG Chromeo 546 (Abcam Ab60317, 1:1000), or anti-mouse antibody coupled to HRP (Jackson Immuno Research Europe, Suffolk, England)]. Appropriate isotype controls were performed in parallel. Subsequently, the cells were mounted with Vectashield containing 4'6-diamindino-2-phenylindole (DAPI; Vector Laboratories, Burlingame, CA, USA) to visualize the nuclei and examined under a Zeiss LSM780 confocal microscope (Carl Zeiss, Jena, Germany). The images were analyzed using the software Zen (Carl Zeiss).

Quantitative Immunocytochemistry (in-Cell Immunoassay) in Non-Permeabilized Rat Sensory Neurons DRG neurons plated on PLL-coated glass coverslips in DMEM:DMEM/F12 1:1 were treated with 10 nM P-CTX-2, 1 µM PbTx-1 or their respective controls for 20 min. In some experiments, cells were pre-treated with 100 µM TTX for 10 min. Cells were then fixed with 2% paraformaldehyde, not permeabilized, and blocked with 5% PBS-milk. PAR-2 immunolabeling was performed using the mouse monoclonal IgG2a anti-PAR-2 antibody SAM11 (ab184673, Abcam, Paris, France, 1:100) then horseradish peroxidase (HRP)-conjugated anti-mouse IgG (Jackson ImmunoResearch Europe, Suffolk, England, 1:10000). Appropriate isotype controls were performed in parallel. After reaction with the HRP substrate, the relative levels of membrane PAR-2 expression were obtained by measuring the absorbance levels at 492 nm, and then normalized to the total amount of cells via Janus Green whole-cell staining.

Determination of Cathepsin S (Cat-S) Activity

The catalytic activity of Cathepsin S (Cat-S) in the co-culture supernatants was determined fluorometrically by the hydrolysis of the specific substrate for Cat-S substrate Ac-Lys-Gln-Lys-Leu-Arg-AMC trifluoroacetate salt. The substrate (100 µM) was preincubated at 37° C. with 0.05 M acetate buffer containing 1 mM DTT and 2 mM EDTA as final concentrations. The reaction was started when equal volumes of the supernatants were added and incubated for 120 min at a final pH of 5.4. The fluorescence (expressed as the relative fluorescence unit, RFU) was measured at 37° C. each 30 minutes with a Flexstation 3™ fluorescence reader at 354 nm excitation and 442 nm emission wavelengths. The same protocol was applied to measure the total cathepsin activity using the fluorogenic substrate Z-Phe-Arg-AMC (Gillet et al. 2009, Vallecillo-Hernandez et al. 2018).

Data Analysis

The substance P (SP) quantification data were expressed as the mean±standard error of the mean (SEM) of at least 3 or 4 separate experiments. The values obtained under the vehicle control conditions (MeOH 0.05%) were subtracted from those obtained under the P-CTX-2 or PbTx-1 conditions. The average levels of released SP (in pg/mL) obtained under the different antagonist conditions were normalized to the average data obtained from P-CTX-2 or PbTx-1 alone, i.e., expressed as a percentage of those obtained under the control conditions as previously described (Le Garrec et al. 2016).

The single cell cytosolic Ca2+ imaging data were expressed as the mean±SEM of at least 3 or 4 separate experiments. The calcium responses are presented as the 340/380 nm fluorescence ratio normalized to the initial ratio F0 using the formula $\Delta F/F0=(F-F0)/F0$, where F is the ratiometric value at a given moment, and F0 is the average of the values before any cell treatments (baseline). For the keratinocytes, the inhibitory effect of each antagonist was assessed based on its ability to decrease the $\Delta F/F0$ values obtained 45 minutes after the P-CTX-2 or PbTx-1 application. For the neuronal cells (heterogeneous population), the percentages of cells responding to P-CTX-2 or PbTx-1 are reported, and the cells were considered to respond if they exhibited a $\Delta F/F0$ increase of at least 0.15. In addition, for the responding neurons, the $\Delta F/F0$ amplitude values during each phase of the P-CTX-2- or PbTx-1-elicited calcium response are reported using the maximum $\Delta F/F0$ for the first and second peaks and the average $\Delta F/F0$ obtained between 20 and 35 minutes, following the P-CTX-2 or PbTx-1 application for the plateau. The antagonist inhibitory effects were assessed using normalized data (percentages of responding cells and amplitude values) from each experiment normalized for each phase, and the average data obtained with the application of P-CTX-2 or PbTx-1 alone were considered 100%.

Based on the time course curves of Cathepsin (Cat-S) activity obtained over 120 minutes, the maximum slope (i.e., the initial velocity of substrate hydrolysis expressed as RFU per minute) was used as the reaction rate and determined for each condition. The results are expressed as a percentage of those obtained under the vehicle control conditions and as the mean±SEM of at least 3 separate experiments.

The statistical analyses were conducted with GraphPad Prism 6.0 (San Diego, CA), and the details are provided in the figure legends. The differences were considered statistically significant if the P value was <0.05.

Example 1: Ciguatoxin P-CTX-2

Results

PAR-2 is Critically Involved in all Phases of the P-CTX-2-Induced Calcium Response in DRG Neurons The present results first show that P-CTX-2 elicited a calcium response in a large proportion of rat sensory neurons (871 of the 1720 analyzed cells, i.e., 50.6±4.3%; raw data not shown). According to the set of cytosolic Ca2+ imaging experiments conducted using DRG neurons, the responses induced by P-CTX-2 were heterogeneous, which is probably related to the different neuron subpopulations. However, the typical calcium responses of the sensory neurons to P-CTX-2 were triphasic, as shown by the patterns presented in FIG. 1a, and could be divided into the following three consecutive phases: 1) a first immediate acute [Ca2+]i (intracellular calcium concentration) increase, named the "first peak", which ended with a partial return to the baseline level followed by 2) a second rapid and sustained [Ca2+]i increase called the "second peak", which ended in 3) a long-lasting calcium "plateau", which almost never returned to the baseline level at the end of the recording. This calcium signal pattern was analyzed in terms of these three distinct phases to chronologically explore the involvement of potential molecular targets using antagonists. The inhibitory effect of specific pharmacological antagonists during each of these phases was assessed by the following two parameters expressed as a percentage of those obtained in P-CTX-2 alone: 1) the normalized percentage of cells responding with such a phase pattern and 2) the normalized amplitude value of the associated Ca2+ signal in cells that continued to respond. The antagonists used included tetrodotoxin (TTX) at two different concentrations to assess the involvement of both TTX-sensitive (TTX-s) and TTX-resistant (TTX-r) Nav channels (Roy and Narahashi 1992, Dib-Hajj et al. 2002, Le Garrec et al. 2016) and GB83, which is a potent specific PAR-2 antagonist (Barry et al. 2010).

The percentage of cells responding to 10 nM P-CTX-2 with the first peak (FIG. 1b) was significantly and equally prevented by 100 µM TTX (34.9±13.4% of cells responding to P-CTX-2 alone), which antagonizes both TTX-s and TTX-r Nav channels, and 300 nM TTX (41.6±12.5%), which inhibits only TTX-s Nav channels (Roy and Narahashi 1992). In the responding cells, the average amplitude of the P-CTX-2-elicited first peak (1.00±0.08; raw data not shown) was significantly and equally decreased by micromolar (53.6±8.0%; FIG. 1c) and nanomolar (47.8±7.2%) concentrations of TTX. These similar inhibitory effects between the two used concentrations of TTX indicate that the first peak is likely mainly mediated by TTX-s Nav channels. Interestingly, GB83, which is a specific antagonist of PAR-2, decreased both the percentage of cells responding (34.5±10.5%; FIG. 1b) and the amplitude value (31.2±4.2%; FIG. 1c) of the P-CTX-2-elicited first calcium peak as efficiently as TTX. These results support the involvement of PAR-2 in the first phase of the calcium response of sensory neurons to P-CTX-2.

Most DRG neurons responding to P-CTX-2 with the first peak (83.2%, i.e., 42.1±4.7% of the studied population) displayed the second peak, which reached an average amplitude of 0.75±0.06 (raw data not shown). The micromolar concentration of TTX and GB83 greatly decreased the percentage of cells responding with a second peak (15.2±8.8% and 16.7±4.1% of cells responding to P-CTX-2 alone, respectively; FIG. 1d), whereas the decrease was less marked following pretreatment with the nanomolar concentration of TTX (36.3±14.8%). In the responding cells, similar to the first peak, the inhibitory effects of the antagonists on the second peak amplitude (FIG. 1e) were correlated with those observed on the percentage of responding cells; 100 µM TTX and GB83 (amplitude reduced to 33.7±3.5% and 27.2±5.0%, respectively) exhibited a more striking inhibitory effect than 300 nM TTX (amplitude reduced to 61.9±16.1%). Since the difference in the inhibitory effects between the µM and nM concentrations of TTX represents the contributory part of TTX-r Nav channels, these data reveal the noteworthy role of TTX-r Nav channels in addition to TTX-s Nav channels in the second phase of the P-CTX-2-evoked calcium signal in DRG neurons. These data also shed light on the prominent contribution of PAR-2 receptor during this phase.

As shown in FIG. 1a, following P-CTX-2 treatment, the intracellular calcium concentration did not return to the basal level after the second peak, which sustained as a long-lasting [Ca2+]i increase (plateau). Most DRG neurons responding to P-CTX-2 with a second peak (67.8%) displayed a plateau. Of the studied population, 28.5±3.4% of the DRG neurons displayed this plateau following P-CTX-2 exposure, and the average amplitude value was 0.45±0.03 (raw data not shown). Similar to the second peak, this plateau phase was abolished in virtually all analyzed cells pretreated with 100 µM TTX or GB83 (4.7±3.1% and 7.9±3.3% of responding neurons compared to P-CTX-2 alone, respectively; FIG. 1f). The nanomolar concentration of TTX was again less effective since 44.9±18.7% of the DRG neurons still responded to P-CTX-2 with a plateau. Among these responding cells, the amplitude values of the plateau were significantly reduced to 50.1±8.7% (FIG. 1g) after GB83 pretreatment. These values were almost equipotently reduced, although non-significantly, by the micromolar concentration of TTX (53.2±1.3%) and poorly decreased by 300 nM TTX (84.8±6.6%). These results suggest that the same molecular mechanisms involved in the second peak, namely, Nav channels and PAR-2, were involved in the sustained calcium plateau, but PAR-2 and TTX-r Nav channels played an even more striking role in this plateau.

In summary, the present results reveal that TTX-s Nav channels play a major role in the early events, i.e., the initiation of the calcium signal elicited by P-CTX-2 in sensory neurons. These data also highlight the additional role of TTX-r Nav channels in the subsequent stages of the calcium signal. Furthermore, since GB83 antagonized the calcium response to P-CTX-2 as early and efficiently as TTX, these data reveal that PAR-2 is a pivotal receptor involved in both the early and late phases of the calcium signal induced by P-CTX-2 in sensory neurons.

In Human Keratinocytes, P-CTX-2 Evokes a Marked Calcium Signal Mediated by the Activation of Nav Channels and PAR-2

Keratinocytes, which are the major cell type in the epidermis, are in contact with intra-epidermal free nerve endings. The direct effect of P-CTX-2 was also explored in primary human epidermal keratinocytes using cytosolic Ca2+ imaging. Interestingly, the keratinocytes exhibited a pronounced biphasic calcium response to 10 nM P-CTX-2 (FIG. 2a). The toxin induced a first low and slow [Ca2+]i increase followed by a more marked and long-lasting [Ca2+]i increase, which never decreased and reached a plateau after approximately 45 min. The average amplitude of this plateau (0.87±0.1; FIG. 2b) was similar to the amplitude of the highest peak (first peak) observed in the sensory neurons, and in contrast to the latter, this plateau was not regulated. In contrast to the DRG neurons, the whole population of keratinocytes from the same patient was activated by P-CTX-2 and displayed the same pattern of [Ca2+]i changes. As illustrated in FIG. 2a, the calcium responses of the primary keratinocytes provided from distinct patients differed, but the two phases were clearly observable in each case. In contrast, the vehicle control (methanol MeOH 0.05%) did not induce any [Ca2+]i change. To assess Nav channel functionality in keratinocytes, the cells were treated with the Nav channel opener veratridine (10 µM), which induced an important [Ca2+]i increase (data not shown), supporting the hypothesis that calcium signals in the keratinocytes could be driven by Nav channel opening. Nav channel and PAR-2 blockers were used to study the involvement of these molecular targets in the P-CTX-2-evoked calcium response in the keratinocytes. Pretreating the cells with the micromolar concentration of TTX or GB83 largely prevented the P-CTX-2-mediated calcium signal, decreasing the average ratio by approximately 70% (from 0.86±0.10 to 0.34±0.11 and 0.33±0.08, respectively; FIG. 2b). These results indicate that P-CTX-2 can directly target human keratinocytes and that Nav channels and PAR-2 are important molecular actors involved in P-CTX-2-evoked calcium signaling in these cells.

PAR-2 activation by canonical agonists (e.g., trypsin) is followed by the cell internalization of the receptor via ß-arrestin-dependent endocytosis (Dery et al. 1999). To confirm the ability of P-CTX-2 to activate PAR-2 in human keratinocytes, confocal imaging experiments were performed to localize PAR-2 in cells after P-CTX-2 exposure. Both P-CTX-2 (10 nM; FIG. 3a) and its functional analog PbTx-1 (brevetoxin-1, 1 µM; FIG. 3b) (Gawley et al. 1992, Dechraoui et al. 1999) could internalize PAR-2, providing further evidence supporting the activation of this receptor by P-CTX-2. Both Nav-activating toxins were able to internalize PAR-2, suggesting that the mechanism depends on Nav activation. Interestingly, PAR-2 internalization was elicited by toxicologically relevant concentrations of P-CTX-2 and PbTx-1 in human keratinocytes. Although keratinocytes are non-excitable cells and supposedly weakly express Nav, the present results suggest that Nav activation by P-CTX-2 (10 nM) and PbTx-1 (1 µM) was sufficient to induce PAR-2 activation in these cells.

Keratinocytes as Full-Fledged Actors in P-CTX-2-Induced SP Release in the Co-Culture A previous study (Le Garrec et al. 2016) reported a novel in vitro model developed to investigate the molecular mechanisms involved in CFP neuro-cutaneous disturbances in which co-cultured DRG neurons and primary keratinocytes released SP and CGRP following P-CTX-2 exposure. In the present study, the co-culture model was subjected to modifications. As described in the Materials and Methods (see section 1), once a great neurite network was formed in the DRG neuron culture, keratinocytes were added and differentiated before the P-CTX-2 exposure in a medium containing a higher (1.4 mM) external calcium concentration. The present results show that the P-CTX-2-induced SP levels released in the optimized co-culture (561.7±97.4 pg/mL) were 8-fold higher than those released in the prototypical model established by Le Garrec et al. 2016 (67.9±22.5 pg/mL; FIG. 4a).

Given the findings that, in keratinocytes, P-CTX-2 can activate PAR-2 and induce calcium signaling, it was investigated whether monocultured keratinocytes could release SP in response to P-CTX-2 and the role of keratinocytes in the P-CTX-2-elicited SP release in the co-culture was assessed. To achieve this aim, the sum of the SP levels released from independent DRG neuron and keratinocyte monocultures was compared with the SP levels released in the co-culture in response to P-CTX-2. Keratinocyte monocultures did not release significant amounts of SP in response to 90-min exposure to 10 nM P-CTX-2 (versus MeOH 0.05%; data not shown). However, the SP release elicited by P-CTX-2 in the co-culture was 6-fold higher than that in the sensory neuron monoculture (598.4±223.3%; FIG. 4b). These results suggest that although monocultures of keratinocytes do not release SP in response to P-CTX-2, they exert a pronounced synergistic effect on the P-CTX-2-evoked SP release in the co-culture.

Nav Channels, PAR-2 and Cat-S are Molecular Effectors of the P-CTX-2-Elicited SP Release in the Co-Culture Selected pharmacological antagonists were used to study molecular mechanisms involved in the P-CTX-2-induced SP release in the optimized co-culture model. The results presented in FIG. 4c show that the pretreatment with 100 µM TTX exerted a greater inhibitory effect than 300 nM TTX on the P-CTX-2-induced SP release (reduced to 29.3±7.3% and 53.1±11.3%, respectively). These data indicate that blocking TTX-s Nav prevented more than half of the release and that the additional blockade of TTX-r Nav resulted in an additional 23.8% inhibition of SP release induced by the toxin, revealing that both types of Nav channels play a role as mediators of the P-CTX-2-induced SP release. The present results further show that GB83 had a striking effect and reduced the release to 15.0±7.9%, indicating that PAR-2 plays a major role in the induced release.

Because the non-protein P-CTX-2 is unlikely to have direct proteolytic activity, it was hypothesized that its PAR-2 activatory effect involves the activity of endogenous PAR-2-activating proteases, such as cysteine proteases. A particular focus was put on Cat-S. A broad-spectrum cysteine protease inhibitor E64 and the Cat-S specific antagonist Z-FL-COCHO were used. E64 significantly reduced the P-CTX-2-elicited SP release to 45.1±8.2%, while Z-FL-COCHO almost completely abolished the release by reducing the SP release to 13.1±6.1% (FIG. 4c). Taken together, given that the best antagonistic effects were obtained with GB83 and Z-FL-COCHO, the present results reveal that P-CTX-2-evoked SP release is predominantly mediated by PAR-2 activation exerted by the cysteine protease Cat-S. This signaling component was confirmed by enzymatic activity measurements in which 90-min exposure to P-CTX-2 (10 nM) or PbTx-1 (2 µM) induced a significant increase in the catalytic activity of Cat-S in the co-culture supernatant (148.9±21.9% and 191.2±33.3%, respectively; FIG. 4e). The co-culture treatment with P-CTX-2 vehicle (MeOH 0.05%) induced a non-significant decrease in Cat-S activity compared to treatment with DMEM:DMEM/F12 (Dulbecco's Modified Eagle Medium:DMEM/Ham's Nutrient Mixture F-12) 1:1 (FIG. 4d). The total cathepsin activity, including cathepsins B and L, measured in supernatants from co-cultures exposed to PbTx-1 (2 µM) using the unspecific substrate Z-Phe-Arg-AMC (Gillet et al. 2009, Vallecillo-Hernandez et al. 2018) was not significantly modified (data not shown).

As an additional experiment, cells (neurons, keratinocytes, alone or in co-culture) were prepared as previously described and treated for 90 minutes with 10 nM of P-CTX-2 or equivalent of methanol. Cathepsin S activity was measured in the supernatant of those cells for 90 minutes. Cathepsin S activity was shows to be increased not only in P-CTX-2-treated sensory neurons and/or glial cells but also in a greater extent in keratinocytes.

TABLE 1

Increase in Cat-S activity in P-CTX-2-treated cells

| | Slope | % increased Cat-S activity |
|---|---|---|
| Keratinocytes alone treated with methanol (control) | 5.27 | 100 |
| Keratinocytes alone treated with P-CTX-2 | 78.74 | 1493 |
| Neurons alone treated with methanol (control) | 134.31 | 100 |
| Neurons alone treated with P-CTX-2 | 192.41 | 143 |
| Co-culture treated with methanol (control) | 66.06 | 100 |
| Co-culture treated with P-CTX-2 | 126.61 | 192 |

Discussion

Both TTX-r and TTX-s Nav are Involved in the Calcium Response to P-CTX-2 in Sensory Neurons In this study, to explore the molecular and cellular mechanisms involved in the P-CTX-2-elicited SP release in the co-culture, cytosolic Ca2+ imaging experiments were performed in rat DRG neurons. The results show that P-CTX-2 induced a typical calcium response in sensory neurons characterized by a first immediate acute increase in [Ca2+]i, followed by a second [Ca2+]i increase that ended in a long-lasting calcium plateau reminiscent of the fast and slow calcium signals elicited by P-CTX-1 in rat myotubes (Hidalgo et al. 2002). Dorsal root ganglia (DRG) contain a heterogeneous population of sensory neurons, and it is presently shown that 50.6% of the analyzed neuronal cells responded to 10 nM P-CTX-2. Previous studies have reported that CTXs affect both TTX-s and TTX-r in sensory neurons (Le Garrec et al. 2016, Inserra et al. 2017, Touska et al. 2017). The separate analysis of the effects of antagonists, including two TTX concentrations, on each step of the P-CTX-2-induced calcium response allowed herein to specify the chronology of the involvement of each studied target. Using this approach, for the first time, the present results show that TTX-s Nav activation by P-CTX-2 mediated the first acute [Ca2+]i increase of the calcium signal pattern observed, which was rapidly and almost completely regulated, whereas the second calcium peak, which was more slowly regulated and ended with a long-lasting plateau, involved the additional activation of TTX-r Nav. Thus, these data indicate that only TTX-s Nav channels initiate the elicited calcium response, while both TTX-s and TTX-r Nav-dependent mechanisms prolong the P-CTX-2-mediated dysregulation of calcium homeostasis that likely leads to neuropeptide release.

In a prototypical co-culture model of sensory neurons and keratinocytes, it was previously shown the predominant role of TTX-r Nav channels in P-CTX-2-induced SP and CGRP release (Le Garrec et al. 2016). However, important inter-experimental variability in the magnitude of the release was observed, likely correlated to the density of the neurite network. Increasing the low external calcium concentration in the activation medium further enhanced the magnitude of the evoked release. In the present study, some modifications were introduced to the model to optimize the elicited release. Keratinocytes were added once the neuronal culture was mature and then differentiated. Moreover, activation by P-CTX-2 was performed in a medium containing a physiological external calcium concentration. These changes led to an 8-fold increase in the SP release induced by P-CTX-2 in the co-culture, allowing for a better exploration of the cellular and molecular mechanisms involved. In this optimized model, the results not only confirm the involvement of TTX-r Nav in the P-CTX-2-elicited SP release in the co-culture but also reveal the important role of TTX-s Nav. Interestingly, the contributory parts of TTX-r and TTX-s Nav in regard to the inhibitory effect caused by their blocking were similar in the SP release (24% and 47%, respectively) and the late phase of the calcium response (21% and 64%, respectively, on the proportion of cells responding with a second peak) induced by P-CTX-2, suggesting that this phase plays a major role in the elicited SP release.

In Response to P-CTX-2, Keratinocytes Exhibit an Unexpected Marked Calcium Signal and Synergistically Contribute to SP Release in the Co-Culture Since CTXs are potent Nav-activating toxins, they are traditionally thought to target only excitable cells. However, CTXs have been shown to activate non-excitable cells expressing Nav, although to a much lesser extent (Pierre et al. 2018). Human keratinocytes from healthy skin have been reported to express the Nav1.5, Nav1.6 and Nav1.7 isoforms, whereas keratinocytes from painful skin exhibit additional Nav1.1, Nav1.2 and Nav1.8 expression (Zhao et al. 2008), i.e., both TTX-s and TTX-r isoforms are expressed in both cases. Furthermore, keratinocytes are increasingly involved in itch and pain transduction (Wilson et al. 2013, Pang et al. 2015, Baumbauer et al. 2015). Thus, it was investigated whether P-CTX-2 could directly target human keratinocytes using cytosolic Ca2+ imaging experiments and whether these cells participate in the SP release in the co-culture model described herein. Surprisingly, the keratinocytes displayed a marked calcium response to the toxin characterized by a slow and very sustained [Ca2+]i increase. This prolonged [Ca2+]i elevation reached a plateau, which amplitude obtained 45 min after the P-CTX-2 application was similar to the maximum amplitudes observed in the transient calcium responses measured in the DRG neurons following P-CTX-2 exposure. These data suggest that keratinocytes have a less efficient regulation system than neuronal cells to extrude excess of internal calcium and, for the first time, identify keratinocytes as cellular targets of CTXs. Furthermore, the present results show that TTX and GB83 strikingly prevented this response, demonstrating that the P-CTX-2-elicited calcium signal in keratinocytes is mediated by Nav channels and PAR-2.

Although P-CTX-2 elicited a marked [Ca2+]i increase in monocultures of keratinocytes, the SP release results show that in the absence of sensory neurons, keratinocytes did not release SP in response to the toxin. Nevertheless, the obvious synergistic role of keratinocytes was demonstrated in the SP release induced by P-CTX-2 in the co-culture (6-fold increase compared to the SP release in the DRG neuron monocultures). The molecular basis of this synergistic effect remains to be studied. Both keratinocytes and sensory neurons express SP and its cognate receptor NK1R and can release SP in an autocrine manner (Bae et al. 1999, Tang et al. 2007). Thus, it is plausible that following P-CTX-2 application, a paracrine SP-evoked positive feedback is present through cross-talk between DRG neurons and keratinocytes. SP released from neurons could elicit SP release in keratinocytes. Vice versa, mediators other than SP released from keratinocytes could also potentiate the P-CTX-2-induced SP release in sensory neurons (Wei et al. 2012) (FIG. 5b).

PAR-2, a New G Protein-Coupled Receptor Involved in the P-CTX-2-Mediated Effects in Sensory Neurons and Keratinocytes This work investigated the role of PAR-2, which is a seven-transmembrane domain receptor coupled to intracellular G proteins, in the effects of P-CTX-2. Indeed, PAR-2 activation in both keratinocytes and peptidergic sensory neurons leads to a [Ca2+]i increase. In the context of inflammation, PAR-2 activation by mast cell tryptase or trypsin has been shown to induce SP and CGRP release (Steinhoff et al. 2000). PAR-2 is also one of the receptors that can be involved in abnormal pain, primarily via serine proteases generated during injury (Liu et al. 2011, Bao et al. 2014). The intra-dermal administration of PAR-2 agonists induces a mast-cell-dependent itch together with cutaneous neurogenic inflammation, notably upon trypsin activation (Steinhoff et al. 2000, Costa et al. 2008). However, itch without any visible skin changes can be elicited after intra-epidermal administration, demonstrating that PAR-2 activation in intra-epidermal nerve terminals and epidermal keratinocytes is sufficient to trigger itch (Arthur and Shelley 1955). To assess the role of this receptor in the P-CTX-2 effects, the specific PAR-2 antagonist GB83 was used. Indeed, this PAR-2 antagonist is known to be effective at a low concentration range in inhibiting responses to both canonical and synthetic agonists (Barry et al. 2010, Lohman et al. 2012). The cytosolic Ca2+ imaging results reveal that PAR-2 plays a major role in both the early and late phases of the calcium signal induced by P-CTX-2 in DRG neurons and the sustained calcium response elicited by the toxin in keratinocytes. In addition, the PAR-2 blockade by GB83 abolished the P-CTX-2-induced SP release in the co-culture model. Therefore, PAR-2 appears to crucially contribute to P-CTX-2-mediated calcium signaling and neuropeptide release.

Finally, a second line of evidence supporting P-CTX-2-mediated PAR-2 activation was provided by confocal imaging of the internalization of the receptor in keratinocytes following P-CTX-2 exposure as previously shown with PAR-2 canonical agonists and activating peptides (DeFea et al. 2000). In addition, the present results show that PbTx-1, whose molecular target is Nav, similar to CTXs (Gawley et al. 1992, Dechraoui et al. 1999), also induced PAR-2 internalization, strongly suggesting that PAR-2 activation induced by the toxins occurs subsequently to Nav activation. This was confirmed by the quantitative immunochemistry results showing that TTX inhibits the decrease of PAR-2 membrane expression induced by the toxins. Taken together, the present findings demonstrate that P-CTX-2 induces PAR-2 activation through a Nav-dependent mechanism, which leads to a calcium response in both DRG neurons and keratinocytes. In sensory neurons, but not keratinocytes, this [Ca2+]i increase is sufficient to induce the release of SP. Therefore, for the first time, the present results unveil that a GPCR, namely, PAR-2, is a key molecular actor in the signaling pathways mediated by CTXs leading to sensory effects. This finding is of major therapeutic interest because there is no specific treatment for CFP sensory disturbances. Besides, without being bound by theory, the Inventors believe that PAR-2 is the molecular link between Nav and TRPA1 involved in cold hypersensitivity during CFP.

Cat-S as Molecular Link Between Nav and PAR-2 Activation Elicited by P-CTX-2

Assuming that the polyether cyclic toxins P-CTX-2 and PbTx-1 are unlikely to have protease activity, it was hypothesized that their ability to activate PAR-2 could be mediated by the release or increase in the activity of endogenous PAR-2-activating proteases. Several cysteine proteases are well-known pruritogenic compounds that are able to induce a [Ca2+]i increase The present results show that the cysteine protease inhibitor E64 (Gillet et al. 2009)—which displays a broad inhibition towards several cysteine proteases—significantly reduced, though incompletely, the P-CTX-2-elicited SP release in the optimized co-culture model, while the Cat-S specific antagonist Z-FL-COCHO almost completely abolished this release. Thus, virtually complete antagonistic effects on P-CTX-2-elicited SP release were obtained with GB83 and Z-FL-COCHO (each alone), which are specific blockers of PAR-2 and Cat-S, respectively. Since Cat-S cleaves and activates PAR-2, the present results indicate that P-CTX-2-evoked SP release is predominantly mediated by PAR-2 activation, which is exerted by cysteine proteases, namely Cat-S in the context of CFP. As a lysosomal cysteine protease, Cat-S exhibits optimal activity at an acidic pH. However, Cat-S remains active extracellularly (i.e., at a neutral pH), where it can be found in membrane-bound and soluble forms (Gillet et al. 2009). Given that both the broad-spectrum cysteine protease inhibitor E64 and the Cat-S specific antagonist Z-FL-COCHO are poorly cell-permeant (Gillet et al. 2009), their efficacy in preventing P-CTX-2-evoked SP release suggests that Cat-S is involved in this effect by acting extracellularly. A second line of evidence supporting extracellular Cat-S activity involvement was provided by measurements of the catalytic activity of the protease in the co-culture supernatant, which was significantly increased following the P-CTX-2 exposure. This increase was also elicited by PbTx-1, suggesting that this effect is achieved via a Nav-dependent mechanism. Taken together, these results show that likely following Nav activation, P-CTX-2 triggers an increase in Cat-S activity, which, in turn, activates PAR-2. This activation subsequently increases [Ca2+]i and, at least in sensory neurons, leads to the release of SP (FIG. 5a).

Example 2: Brevetoxin PbTx-1

Results

PbTx-1 Induces a Calcium Response Similar to P-CTX-2 in Sensory Neurons

PbTx-1 induces a typical calcium response in sensory neurons. This extended calcium response is biphasic. Immediately post-injection of 1 μM of PbTx-1, the intracellular calcium ([Ca]$_i$) strongly increased, reaching an amplitude of 1.196±0.08 and is rapidly regulated. This first transient is called the first peak. The second peak reached progressively an amplitude of 1.256±0.08 and continued by a long-lasting phase named the plateau reaching an amplitude of 0.492±0.02 (data not shown).

Nav Channels, Cathepsin S and PAR-2 are Involved in the PbTx-1 Signaling Pathway in Sensory Neurons Effects of antagonists were assessed on the PbTx-1-induced calcium signal. Two parameters were recorded for each phase: the normalized percentage of responding cells to PbTx-1 and the associated normalized amplitude of the response, with or without antagonist pre-treatment. FIGS. 6A, 6C and 6E represents the normalized percentage of responding cells of the first peak, second peak and the plateau respectively. FIGS. 6B, 6D, 6F show the associated normalized amplitude values. Each solvent was also tested (data not shown). In order to study whether that PbTx-1 is a good substitute of P-CTX-2 and to chronologically explore the involvement of TTX-s and TTX-r Nav, PAR-2 and cathepsin S, calcium imaging was used.

300 nM of TTX and 100 μM of TTX significantly decreased the percentage of cells responding to PbTx-1 with the first peak (65.20±14.50%; 34.40±21.24% respectively), strongly with the second peak (26.6±6.56%; 2±2%) and with the plateau (73±8.13%; 11.40±4.6%) (FIGS. 6A, 6C and 6E). In addition, TTX 100 μM significantly and strongly decreased the amplitude of the second peak (3.4±3.4%) (FIG. 6D). These results strongly suggest that Nav channels are involved in the whole of the calcium signal induced by the PbTx-1 in sensory neurons. Moreover, the involvement of TTX-r and TTX-s Nav channels were assessed by comparing the effects of TTX 300 nM and TTX 100 μM Interestingly, statistical study indicates a significant difference between each parameter recorded in presence of TTX 300 nM and of TTX 100 μM except in the amplitude values of the plateau. These results suggest the additional involvement of Nav TTX-r in the whole calcium signal.

Z-FL-COCHO and GB83 significantly decreased the percentage of cells responding of the first peak (48.2±11.1%; 75.7±7.28% respectively), of the second peak (45.2±11.1%; 48.9±7.38% respectively) and of the plateau (41.0±13.8%; 37.7±7.7% respectively) induced by the PbTx-1 (FIGS. 6A, 6C and 6E). PbTx-1 did not significantly modify the amplitude values (FIG. 6B, 6D, 6F). Together, those data suggest the critical role of Z-FL-COCHO and GB83 in the PbTx-1 signaling pathway in sensory neurons as previously showed with the P-CTX-2 signaling in the same model (see Example 1).

PbTx-1 Induced Cathepsin S and PAR-2-Dependent Substance P (SP) Release from Co-Cultured Sensory Neurons and Keratinocytes Following 90 minutes of treatment with different concentrations of PbTx-1, the ability of PbTx-1 to induce SP release was assessed (FIG. 7A). No cytotoxicity was observed for each concentration assessed by MTT assay (data not shown).

At 1 µM, PbTx-1 significantly increased the SP release (363.3±87.3%), 2 µM of PbTx-1 significantly increased the SP release (418±119%) and 5 µM of PbTx-1 significantly increased the SP release (465±89.9%) (FIG. 4A). Therefore, as demonstrated above for P-CTX-2, PbTx-1 is also able to induce a strong SP release from a co-culture model of sensory neurons and human keratinocytes.

To assess the involvement of PAR-2 and cathepsin S in the PbTx-1-induced SP release, the effects of specific antagonists GB83 and Z-FL-COCHO were assessed, individually. Both antagonists significantly decreased the PbTx-1-induced SP release to 40.9±7.4% and to 80.4±4.1%, respectively (FIG. 7B). These results show that both cathepsin S and PAR-2 are involved in the PbTx-1-induced SP release. Therefore, demonstrated above for P-CTX-2, PbTx-1 is also able to induce a cathepsin S- and a PAR-2-dependent SP release from a co-culture model of sensory neurons and human keratinocytes.

In order to determine whether cathepsin S and PAR-2 belong to the same signaling pathway in PbTx-1-induced SP release (i.e. whether cathepsin S is responsible of PAR-2 activation), the inhibitory effect of GB83/Z-FL-COCHO was compared to GB83 alone. The inhibitory effect of GB83/Z-FL-COCHO (39.5±6.9%) was not significantly different of the inhibitory effect of the pre-treatment GB83 alone (45.3±6.9%) (FIG. 7C). These data suggest that cathepsin S and PAR-2 belong to the same pathway (i.e cathepsin S is responsible for PAR-2 activation).

Hence, as demonstrated with P-CTX-2, PbTx-1 is able to induce SP release from a cocultured model through a cathepsin S and PAR-2 mechanism.

P-CTX-2- and PbTx-1-Induced PAR-2 Internalization is $Na_v$-Dependent

The effects of PbTx-1 on PAR-2 membrane expression was assessed, as well as the underlying mechanisms in non-permeabilized sensory neurons. At the resting state, PAR-2 is largely expressed at the plasma membrane. After 1 µM of PbTx-1 treatment, membrane expression of PAR-2 significantly diminished to 73.5±1.7%, whereas pre-treatment by 100 µM of TTX prevented the decrease of the membrane PAR-2 expression (95.3±4.9%) (FIG. 8A). PAR-2 internalization after P-CTX-2 treatment was also explored in sensory neurons (FIG. 8B). P-CTX-2 induced a significant decrease in the membrane expression of PAR-2 (42.3±7.9%), whereas pre-treatment with 100 µM of TTX prevented the decrease of the membrane PAR-2 expression (92.7±1.3%) (FIG. 8B). These results indicate the $Na_v$-dependence of PAR-2 activation by PbTx-1.

Actors of Both Canonical and Biased PAR-2 Signaling Pathways are Involved in the Calcium Response Induced by PbTx-1 from Sensory Neurons PAR-2 signaling pathway is complex and multiple including canonical and biased signaling. In order to decipher PAR-2 downstream signaling pathway induced by PbTx-1, the involvement of actors in the canonical and the biased PAR-2 signaling pathways were further studied.

Study of pathway downstream of PAR-2 led to test a specific antagonist of PKC named BimX, a specific antagonist of PKA named H89, and a specific antagonist of IP3r named Xestospongin C. Both antagonists did not decrease the calcium parameters recorded in the first peak (FIG. 9A) but significantly decreased the percentage of responding cells to PbTx-1 of the second peak (67.7±7.5%; 64.8±6.8%; 62.5±14.7% respectively) (FIG. 9C). In addition, the percentage of responding cells of the plateau in the H89 condition is significantly decreased (64.8±6.8%) (FIG. 9E). No significant modification of any amplitude values was shown in each phase for those antagonists (FIGS. 9B, 9D, 9F). Taken together, these results suggest the involvement of PKC and IP3r which belong to the canonical PAR-2 pathway and the involvement of PKA which belong to the biased PAR-2 pathway.

To study the involvement of TRPV4 known to be sensitized by both canonical and biased PAR-2 pathways, HC-067047 was used as an antagonist of TRPV4. HC-067047 significantly decreased the PbTx-1-induced calcium response of the first peak (59.4±11.5%), the second peak (35.6±11.5%) and the plateau (35.0±16.1%) (FIGS. 9A, 9C and 9E). No significant modification of amplitude values was recorded in each phase (FIGS. 9B, 9D and 9F).

Actors of Both Canonical and Biased PAR-2 Signaling Pathways are Involved in the SP Release Induced by PbTx-1 in the Coculture Model Based on the calcium experiment observations, the effects of PKC, PKA, IP3r and TRPV4 antagonists were explored in the PbTx-1-induced SP release in the co-culture supernatants. PbTx-1-induced SP release was significantly decreased by the BimX pre-treatment (37.4±5.9%), by the H89 pre-treatment (36±8.1%), by the Xestospongin C pre-treatment (35.5±9.7%) and by the HC-067047 pre-treatment (58.7±14.5%) respectively (FIG. 10A). These findings suggest that PKC, PKA, IP3r and TRPV4 are involved in the SP release induced by PbTx-1 in the coculture model.

It is admitted that TRPV4 is sensitized by PAR-2, it was thus tested whether, in the PbTx-1-induced SP release, TRPV4 and PAR-2 belong to the same pathway. Pre-treatment with 5 µM of GB83 alone or 10 µM of HC-067047 alone significantly prevented PbTx-1-induced SP release (47±8.2% and 41.3±14.5% respectively) (FIG. 10B). Pre-treatment with GB83 and HC-067047 also significantly decreased the PbTx-1 induced SP release to 34.7±9.2% (FIG. 10B). Pre-treatment with a combination of GB83 and HC-067047 did not induce additional decrease of PbTx-1-induced SP release compared to GB83 alone and HC-067047 alone. Taken together, these results suggest that PAR-2 and TRPV4 belong to the same signaling pathway in the PbTx-1 induced SP release (i.e. that TRPV4 may be sensitized in a PAR-2-dependent manner).

Discussion

Currently, CTXs are not commercialized but their abundant similarities with PbTxs place PbTxs as an interesting tool to study neurotoxins signaling pathway on sensory neurons. The objectives of this study were to 1) identify whether PbTx-1 is a good substitute to study CTX signaling pathway in sensory neurons especially the mechanisms involved in SP release and the downstream activation of PAR-2 2) explore and clarify the induced downstream PAR-2 signaling pathways after PbTx-1 treatment in sensory neurons. This study demonstrates that, similarly to P-CTX-2, cathepsin S and PAR-2 are key actors in PbTx-1-induced calcium response and SP release. The present results show that PAR-2 activation is consecutive to $Na_v$ activation, and also demonstrate the involvement of both canonical and biased PAR-2 signaling in sensory neurons treated by PbTx-1.

Similar Calcium Signal Induced by P-CTX-2 and PbTx-1 in Sensory Neurons

Calcium response profile induced by the PbTx-1 brevetoxin in sensory neurons showed 3 phases, like P-CTX-2. The percentage of responding cells to PbTx-1 from sensory neurons in rat DRG was also similar to that with PTX2. In addition, the profiles of calcium response induced by PbTx-1 1 μM in sensory neurons highlighted different subpopulations of neurons in the culture.

Involvement of Both TTX-r $Na_v$ and TTX-s $Na_v$ in the Calcium Response Induced by PbTx-1

Study of calcium imaging allowed to decipher the chronology of the calcium response induced by PbTx-1. 300 nM of TTX and 100 μM of TTX significantly decreased the PbTx-1 calcium response in DRG neurons. Statistical analysis highlights evidence of the additional implication of $Na_v$ TTX-r and suggests the biological relevance of $Na_v$ TTX-r role. $Na_v$ TTX-r, including $Na_v$ 1.8 and $Na_v$ 1.9. The present results suggest that TTX-r $Na_v$ plays an additional role in PbTx signaling pathway in sensory neurons, like CTX.

Involvement of Cathepsin S and PAR-2 in PbTx-1-Induced Calcium Response and SP Release The present study demonstrates, for the first time, that PbTx-1 is able to induce SP release. SP release is shown to be dependent of the PbTx-1 concentration used. Cathepsin S and PAR-2 are critically involved in the $[Ca^{2+}]_i$ increase not only in the P-CTX-2 induced SP release, but also and in the PbTx-1-induced SP release. Like for P-CTX-2, the results show that cathepsin S activates PAR-2, after treatment by PbTx-1. Cathepsin S and PAR-2 are thus novel actors involved in the PbTx-1-induced SP release. PbTx-1 is a good substitute to further study CTX pathways occurring downstream of PAR-2 in sensory neurons.

Canonical and Biased PAR-2 Signaling Pathways are Involved in PbTx-1-Induced Calcium Response and SP Release Distinct pathways are involved downstream of PAR-2 called canonical and biased pathways. Involvement of several actors belonging to PAR-2 canonical pathway including PKC, IP3r and actors belonging to the PAR-2 biased pathway including PKA were studied. In addition, TRPV4 is known to be sensitized by both PAR-2 canonical and biased pathways. The results showed that both actors mentioned above are implicated in PbTx-1-induced calcium response.

Results of PbTx-1-induced SP release experiments conducted with the PKC inhibitor BimX, the PKA inhibitor H89, the IP3r inhibitor Xestospongin C and the TRPV4 inhibitor HC-067047 suggested the involvement of PKC and IP3 indicating canonical PAR-2 pathway whereas involvement of PKA signs PAR-2 biased pathway. In addition, TRPV4 is known to be sensitized by both PAR-2 signaling pathways. This result suggests the involvement of TRPV4 in both signaling pathway downstream of PAR-2 activation by PbTx-1. Once sensitized, TRPV4 could response to ineffective stimuli in normal conditions and enhance the neuron hyperexcitability.

Interestingly, the results showed IP3 involvement in the PbTx-1-induced calcium release and SP release. However, IP3 involvement might be PAR-2-independent (i.e. Cay-dependent) as suggested in the scientific literature.

CONCLUSION

The present study highlights, for the first time, the critical role of PAR-2 and cathepsin S in the CTXs and PbTxs signaling in sensory neurons and keratinocytes.

More particularly, the present data clearly show that:

the exposure of keratinocytes or sensory neurons to PbTx-1 or P-CTX-2 resulted in an [Ca2+]i increase, which involved $Na_v$ and PAR-2 activation. In that regard, it should be noted that CTXs and PbTxs share the same site of binding on Nay channel (Dechraoui et al., 1999; Lombet et al., 1987), and induced a partial PAR-2 internalization. This internalization occurred in a $Na_v$-dependent manner;

the exposure of the neuro-cutaneous co-culture to PbTx-1 or P-CTX-2 resulted in a significant increase in the catalytic activity of Cat-S and subsequent PAR-2 activation, which promoted the SP release. Of note, global cathepsin activity was not modified in presence of PbTx-1 or P-CTX-2 (data not shown). This highlights the specific role of Cat-S as a molecular link between Nav and PAR-2 activation elicited by PbTx-1 or P-CTX-2;

the use of PAR-2 or Cat-S inhibitor reduced the effects induced by P-CTX-2 or PbTx-1. In particular, such inhibitors were shown to reduce the calcium response as well as the SP release;

Both the canonical and the biased PAR-2 signaling pathways are involved in PbTx-1 induced calcium response and SP release.

Within the nervous system, Cat-S is known to be expressed mainly in microglial cells and macrophages, and in low levels in DRG neurons. However, the scientific literature has reported that Cat-S and other cathepsins are up-regulated in sensory neuron axons and Schwann cells following nerve ligation or neurotoxic exposure. Similarly, human keratinocytes can display a striking Cat-S activity after stimulation. Following P-CTX-2 exposure, Cat-S activity is increased in the co-culture model, which contains keratinocytes, DRG neurons and Schwann cells. P-CTX-2 induces PAR-2 activation in keratinocyte and DRG neuron monocultures, suggesting that Cat-S could originate from both cell types in the co-culture. This was confirmed by the measurement of Cat-S activity in independent monocultures of DRG neurons and keratinocytes (Table 1). Following P-CTX-2 exposure, Cat-S from keratinocytes could activate PAR-2 not only in keratinocytes but also in co-cultured sensory neurons. Cat-S from keratinocytes may thus mediate the synergistic effect of these cells in the P-CTX-2-evoked SP release from the co-culture. These data suggest for the first time that Cat-S and PAR-2 are molecular mediators involved in communication between keratinocytes or possibly Schwann cells and sensory neurons following exposure to PbTxs or CTXs.

The neuropeptides SP and CGRP initiate neurogenic inflammation and the recruitment of leucocytes, including macrophages and microglial cells, perineurally and in the spinal cord. Interestingly, Cat-S, PAR-2 and NK1R are expressed in these cells and lead to neuro-inflammatory responses. Given that the present work showed that Cat-S and PAR-2 are key mediators of P-CTX-2/PbTx-1-induced SP release, the Inventors believe, though without being bound by theory, that neuro-immune interactions could potentially occur during CFP or brevetoxin poisoning, and, by amplifying and maintaining neuronal activation, could contribute to sensory troubles occurring in humans following acute exposure to CTXs or PbTxs.

In summary, the results presented herein identify that Cat-S and PAR-2 are new molecular mediators involved in the $[Ca^{2+}]_i$ increase and subsequent SP release induced by a CTX or PbTx from co-cultured keratinocytes and sensory neurons. These findings indicate that Cat-S and PAR-2 are promising pharmacological targets for specifically relieving distressing sensory disorders occurring during CFP or brevetoxin poisoning. In addition, while CTXs or PbTxs are well-known to primarily target neurons, these results indicate that they are also able to directly target keratinocytes through $Na_v$ activation. Finally, the present data demonstrate that these non-excitable cells are able to potentiate CTX/PbTx-induced neuronal activation, suggesting neuro-epithelial communication following exposure to CTXs or PbTxs. Cat-S, PAR-2 and SP are candidate mediators of such interactions, or even neuro-glial or neuro-immune interactions, which could explain the sensory disturbances occurring during CFP or brevetoxin poisoning.

REFERENCES

Abraham A et al. (2008). Toxicon 52:237-245.
Al-Ani et al. (2002). J Pharmacol Exp Ther; 300(2):702-708
Arthur R P and Shelley W B (1955). J Invest Dermatol 25:341-346.
Bae S et al. (1999). Biochem Biophys Res Commun 263:327-333.
Bagnis R and Legrand A-M (1987). Progress in Venom and Toxin Research: proceedings of the First Asia-Pacific Congress on Animal, Plant and Microbial Toxins held in Singapore, Jun. 24-27, 1987, University of Singapore. P. Gopalakrishnakone et al., Singapore, pp 372-384.
Bao Y et al. (2014) Expert Opin Ther Targets 18:15-27.
Barry G D et al. (2010). J Med Chem 53:7428-7440.
Baumbauer K M et al. (2015). eLife 4:e09674.
Boitano S et al. (2015). Br J Pharmacol.; 172(18):4535-4545.
Cameron J and Capra M F (1993). J Toxicol Clin Toxicol 31:571-579.
Carlson K E et al. (2002). Drug Discovery Today Technologies 9(1): e33-e39.
Chateau-Degat M-L et al. (2007). Am J Trop Med Hyg 77:1170-1175.
Chen T L et al. (2011). Journal of Biomedical Science; 18:43.
Cho et al. (2015). Bioorganic & Medicinal Chemistry, 23: 7717-7727.
Chéret J et al. (2014). J Dermatol Sci 74:193-203.
Costa R et al. (2008). Br J Pharmacol 154:1094-1103.
Dechraoui M Y et al. (1999). Toxicon 37:125-143.
Dechraoui M Y et al. (2007). Toxicon 49:100-5
DeFea K A et al. (2000). J Cell Biol 148:1267-1281.
Derouiche F et al. (2000). Rev Neurol (Paris) 156:514-516.
Déry O et al. (1999). J Biol Chem 973 274:18524-18535.
Dib-Hajj S et al. (2002). Trends Neurosci 25:253-259.
Dickey R W et al. (1999). Nat Toxins 7: 157-165.
Diogene J et al. (2017). Sci Rep. 2017 Aug. 15; 7(1):8240.
Dommisch H et al. (2007). Infect Immun., 75(9):4326-33.
Elmariah S B et al. (2014). PloS One 9:e99702.
Gawley R E et al. (1992). Toxicon Off J Int Soc Toxinology 30:780-785.
Ge L et al. (2003). J Biol Chem 278:34418-34426.
Gillet L et al. (2009). J Biol Chem 284:8680-8691.
Gingold D B et al. (2014). Environ Health Perspect 122: 580-586.
Hamilton et al. (2002a). Toxicon 40: 1347-1353.
Hamilton et al. (2002b). Toxicon 40: 685-693.
Hidalgo J et al. (2002). Br J Pharmacol 137:1055-1062.
Holz G G, Dunlap K, Kream R M (1988). J Neurosci Off J Soc Neurosci 8:463-471.
Ikehara T et al. (2017). Toxins, 9(7) pii: E205.
Inserra M C et al. (2017). Sci Rep 7: article number 42810.
Isbister G K, Kiernan M C (2005). Lancet Neurol 4:219-228.
Katunuma N et al. (1999). FEBS Letters 458:6-10.
Kayssi A et al. (2007). J Physiol 580:977-991.
Lawrence J. et al. (2011). Assessment and management of biotoxin risks in bivalve molluscs. Food and Agriculture Organization of the United Nations. ISBN 978-92-5-107003-1, in particular pages 51 to 98.
Le Gall-Ianotto C et al. (2012). Neuroscience 210:47-57.
Le Garrec R et al. (2016). Toxicon Off J Int Soc Toxinology 116:4-10.
Lee Dutra A et al. (2011). Expert Opin. Ther. Patents, 21(3):311-337.
Lewis R J et al. (1991). Toxicon Off J Int Soc Toxinology 29:1115-1127.
Lewis R J et al. (2009). Toxicon 54:62-66.
Lieu T et al. (2016). British Journal of Pharmacology. DOI:10.1111/bph.13554
Liu Q et al. (2011). Sci Signal 4(181): ra45. Doi:10.1126/scisignal.2001925.
Lohman R-J et al. (2012). FASEB J Off Publ Fed Am Soc Exp Biol 26:2877-2887.
Lombet A et al. (1987). FEBS Lett 219:355-359.
Manger R et al. (1995). J AOAC Int 78:521-527.
Moss C R et al. (2015). Neurosci Lett 589:13-18.
Pang Z et al. (2015). Pain 156:656-665.
Pearn J (2001). J Neurol Neurosurg Psychiatry 70:4-8.
Persson A-K et al. (2010). Mol Pain 6:84.
Pierre O et al. (2018). Toxicon 149:6-19.
Ramachandran R et al. (2009). Mol Pharmacol 76:791-801.
Reddy V B, Lerner E A (2010). Br J Dermatol 163:532-535.
Riese R J et al. (1998). The Journal of Clinical Investigation 101(11):2351-2363.
Roy M L, Narahashi T (1992). J Neurosci Off J Soc Neurosci 12:2104-2111.
Schnorf H et al. (2002). Neurology 58:873-880.
Schwarz G et al. (2002). J Invest Dermatol 119:44-49.
Sevigny L M et al. (2011). Proc Natl Acad Sci USA; 108(20):8491-8496.
Skrlec et al. (2015). Trends in Biotechnology; 33(7): 408-418.
Steinhoff M et al. (2003). J Neurosci Off J Soc Neurosci 23:6176-6180.
Steinhoff M et al. (2000). Nat Med 6:151-1188 158.
Stevens M et al. (2011). Front Pharmacol. 9; 2:71
Suen J Y et al. (2014). British Journal of Pharmacology., 171: 4112-4124.
Tang H-B et al. (2007). Mol Pain 3:42.
Tato M et al. (2017). Nature Scientific Reports 7:2775, pages 1-15.
Touska F et al. (2017). Mar Drugs 15: pii: E269. doi: 10.3390/md15090269.
Thurmond R L et al. (2004). The Journal of Pharmacology and Experimental Therapeutics, 308(1): 268-276.
Tsai J Y et al. (2014). J Enzyme Inhib Med Chem, 29(4): 538-546.
Vallecillo-Hernandez J et al. (2018). Scientific Reports 8:3593.
Walker B et al. (2000). Biochemical and Biophysical Research Communications 275, 401-405.
Wei T et al. (2012). J Neuroinflammation 9:181.
Wiener J J M et al. (2010). Current Topics in Medicinal Chemistry, 10: 717-732.
Wilson S R et al. (2013). Cell 155:285-295.
Xu W et al. (2015). J Chem Inf Model. 26; 55(10):2079-84.
Yau M K et al. (2016a). Expert Opinion on Therapeutic Patents 26(4): 471-483. I
Yau M K et al. (2016b). ACS Medicinal Chemistry; 2016, 7(12): 1179-1184.
Yau M K et al. (2013). J Med Chem 56:7477-7497.
Zhao P et al. (2008). Pain 139:90-105.
Zhu J et al. (2017). Oncotarget. 27; 8(37):61810-61823.

The invention claimed is:

1. A method for treating a sensory neuropathy induced by poisoning with a marine sodium-activating neurotoxin in a subject in need thereof, said method comprising administering a therapeutically effective amount of a protease-activated receptor-2 (PAR-2) inhibitor to the subject.

2. The method according to claim 1, wherein said sensory neuropathy is pruritus, paresthesia, dysesthesia, allodynia, myalgia, arthralgia, dysuria, dental pain, or a combination thereof.

3. The method according to claim 1, wherein said sensory neuropathy is mediated via activation of a voltage-gated sodium channel (VGSC) by the marine sodium-activating neurotoxin.

4. The method according to claim 1, wherein said marine sodium-activating neurotoxin binds to an alpha subunit of a voltage-dependent sodium channels.

5. The method according to claim 1, wherein said marine sodium-activating neurotoxin comprises a ciguatoxin (CTX), a brevetoxin (PbTx), an active metabolite thereof, or a combination thereof.

6. The method according to claim 1, wherein said PAR-2 inhibitor is a PAR-2 full antagonist or a PAR-2 biased antagonist.

7. The method according to claim 1, wherein said PAR-2 inhibitor is selected from the group consisting of a small molecule, a peptide, a polypeptide, a polynucleotide, and a combination thereof.

8. The method according to claim 1, wherein said PAR-2 inhibitor is selected from the group consisting of GB83, GB88, and a derivative thereof.

9. The method according to claim 1, wherein said PAR-2 inhibitor inhibits Cathepsin-S-mediated PAR-2 signaling.

10. The method according to claim 1, wherein said PAR-2 inhibitor is selected from the group consisting of the Cathepsin S inhibitor Cbz-Phe-Leu-COCHO, and a derivative thereof.

11. The method according to claim 1, wherein said PAR-2 inhibitor is in a pharmaceutical composition.

12. The method according to claim 2, wherein said sensory neuropathy is mediated via activation of a VGSC by the marine sodium-activating neurotoxin.

13. The method according to claim 2, wherein said marine sodium-activating neurotoxin binds to an alpha subunit of a voltage-dependent sodium channel.

14. The method according to claim 3, wherein said marine sodium-activating neurotoxin binds to an alpha subunit of a voltage-dependent sodium channel.

15. The method according to claim 2, wherein said marine sodium-activating neurotoxin comprises a ciguatoxin (CTX), a brevetoxin (PbTx), an active metabolite thereof, or a combination thereof.

16. The method according to claim 1, wherein said PAR-2 inhibitor is a PAR-2 full antagonist.

17. The method according to claim 7, wherein said PAR-2 inhibitor is selected from the group consisting of a pepducin, an antibody, a RNAi, an aptamer, and a combination thereof.

* * * * *